United States Patent [19]

Berrens

[11] Patent Number: 5,667,979
[45] Date of Patent: Sep. 16, 1997

[54] USE OF SPECIFIC PROPERTIES OF ALLERGENS, ALLERGENS FROM ANIMAL OR BOTANICAL SOURCES AND METHODS FOR THEIR ISOLATION

[75] Inventor: Lubertus Berrens, Utrecht, Netherlands

[73] Assignee: Laboratorios Leti S.A., Barcelona, Spain

[21] Appl. No.: 461,642

[22] Filed: Jan. 5, 1990

[30] Foreign Application Priority Data

Jan. 5, 1989 [EP] European Pat. Off. ............ 89200027

[51] Int. Cl.$^6$ .............. C12Q 1/34; C12Q 1/37; C12Q 1/44; G01N 33/573
[52] U.S. Cl. .............. 435/7.4; 435/18; 435/19; 435/23; 435/24; 436/513; 436/518
[58] Field of Search .............. 435/7.4, 23, 24, 435/18; 436/513, 518

[56] References Cited

PUBLICATIONS

Maddison et al–Chem. Abst. vol. 82 (1975) p. 71153f.
Willadsen –Chem. Abst. vol. 86 (1977) p. 87479k.
Ole–Moi Yoi –Chem. Abst vol. 88 (1978) p. 17948e.
Meier et al. "Anaphylactic Release of a Prekallikrein Activator from Human Lung In Vitro" Jo. Clin. Invest. vol. 72 Aug. '83 pp. 574–581.
Stewart et al., "Immunochemical and enzymatic analyses of extracts of the house dust mite Dermatophagoides pteronyssinus" J. Allergy Clin Immunol. vol. 77 No. 1 Part 1 pp. 14–24.
Berrens et al. "The Atopen: A Rehabilitation" Ann. of Allergy. vol. 36, May 76 pp. 351–361.
"Characterization of Types of Enzymatic Activity in Sonatic Extracts of Selected Fungi, Thermophillic Actinomycetes and Pollen by Immunoelectrophoresis", Biological Abstracts, vol. 62, No. 6, 1976, Abstract No. 29212, By P. Kimura et al., pp. 2890–2891.
"Immunochemical and Enzymic Analyses of Extracts of the House Dust Mite Dermatophagoides Pteronyssinus", Chemical Asbtracts, vol. 104, No. 15, Apr. 1986, Abstract No. 127808r, By G. Stewart et al., pp. 523–524.
"2.1. The Principle of Affinity Chromatography", Affinity Chromatography, 1986, p. 6.
"Analysis of Commercial Pollen Extracts by Enzyme Determination: 1. Comparison of Radioallergosorbent Titration Inhibition Assay and Enzyme Titration for Orchard Grass (Dactylis glomerata), rye grass (Ambrosia elatior) pollen extracts", Biological Abstracts, vol. 71, No. 7, 1981, Abstract No. 42673, By J. Bousque et al., p. 4474.
"Enzyme Determination and RAST Inhibition Assays for Orchard Grass (Dactylis glomerata): a comparison of commercial pollen extracts", Chemical Abstracts, vol. 89, No. 21, Nov. 1978, Abstract No. 177776w, By J. Bousquet et al., p. 426.
"Allergens in Bee Venom. III. Identification of Allergen B of Bee Venom as an Acid Phosphatase", Chemical Abstracts, vol. 87, No. 7, Aug. 1977, Abstract No. 51463g, By D. Hoffman, p. 325.

Primary Examiner—David Saunders
Attorney, Agent, or Firm—Young & Thompson

[57] ABSTRACT

It was found that atopic allergens have enzymatic properties, in particular the properties to hydrolyze amide and/or ester linkages. These properties may be used for various purposes, e.g. for analysis of samples, standardization of pharmaceutical compositions and also for the preparation of the allergens in a pure form.

9 Claims, 7 Drawing Sheets

USE OF SPECIFIC PROPERTIES OF ALLERGENS, ALLERGENS FROM ANIMAL OR BOTANICAL SOURCES AND METHODS FOR THEIR ISOLATION

FIELD OF THE INVENTION

The present invention relates to the use of specific properties of allergens, to allergens from animal or botanical sources and methods for their isolation.

BACKGROUND OF THE INVENTION

Hypersensitivity in human beings to certain substances in the environment may manifest itself in the form of several different disease symptoms. Of these, the syndromes of allergic bronchial asthma, neurodermatitis, vasomotor rhinitis, hay fever (or pollinosis) and food allergies are among the most widely known. Despite the fact that in any human population in any geographical location the exposure to the inciting agents (or "allergens") is about equal for each individual, it is nevertheless a fairly constant proportion of about 10% of any given population that really develops manifest disease symptoms. This polar group of the human population is identified as being "atopic", meaning that the afflicted individuals have a genetically determines predisposition to respond with disease symptoms to "allergens" in the environment, in contrast to the non-atopic population which responds only at much higher levels of exposure, or not at all. Current scientific theory holds that manifest allergic disease in atopic subjects is caused by the interaction of such environmental allergens with specific antibodies, so-called immunoglobulins of the IgE-isotype, which recognize the allergen as an individual macromolecular entity or, in current terminology, as an "antigen". Since this IgE-class antibody is indeed predominantly found in the blood and tissues of atopic people, the inherited physiological condition of "atopy" is considered to be primarily an inborn abnormality of the immunological defense system, causing atopic people to be "high IgE-responders".

The medical treatment of human disease normally aims at combatting the ultimate physiological effects of the chain-reactions initiated by the allergen-IgE interaction, and therefore relies on antihistaminic drugs, cholinergic antagonists or adrenergic agonists, on repeated injections with the offending allergen to induce a shift of the antibody response in the direction of presumed "protective" IgG-antibodies and, prophylactically, on identifying and eliminating the source of the particular allergen(s) in the patient's environment. The science and technology of identifying and quantifying the causative allergens in a patient's direct environment, i.e. in the home or workplace, has remained underdeveloped. Further technologies in this field are badly needed in order to provide each individual patient or group of patients with sound advice on "sanitation" of their environment and reduction of the allergen load, prior to taking drugs for alleviating the symptoms. Such measures depend on the techniques available for allergen detection, and the development of these derives from current scientific insight into their nature and mode(s) of action.

The current viewpoint of human allergic disease of the so-called "immediate-type" (Type I in immunological classification) hinges on the structural concept of allergens being recognized as molecular entities (or as "antigens") by specific IgE-antibodies. The clinical detection and identification of allergens by their capacity to induce strong wheal and flare (urticarial and erythemal) reactions when injected into the skin of specifically sensitized atopic patients for obvious reasons is too cumbersome to allow adequate monitoring of the allergenic potential of the environment. Laboratory methods developed for this purpose have therefore relied on elaborate and expensive immunochemical techniques for the identification and quantification of allergens in extracts of environmental substrates by means of binding studies to IgE-antibodies in individual or pooled human blood serum samples from allergic individuals.

The major allergenic substances for atopic people derive from components in the dust accumulating in houses. Many different organisms contribute to this allergen load, in particular mites and other arthropods, insects, yeasts and moulds and, in the relevant seasons, wind-distributed pollen grains from grasses, trees and weeds from the outside environment. In some dwellings, allergens shed with the skin scales, dried saliva or urinary constituents from animal pets like cats, dogs, birds and other animals may contribute substantially to the allergen load in an individual's personal environment. In order to identify each and every one of these different allergens by techniques based on the binding of specific IgE-antibodies, a very large variety of blood serum samples of allergic individuals would have to be available. This particular prerequisite will continue to hamper the development of adequate control measures of the allergic environment of man.

In an attempt to quantify the contribution of the so-called house dust mites *Dermatophagoides pteronyssinus* and *D. farinae*, which live in house dust and excrete highly potent inhalant allergens for man, it has been proposed to quantify the nitrogenous excretion product guanine in samples taken from the dust. A technological procedure has been made available based on this principle and has been described in the scientific and patent literature EP 0 144 820, 0 152 068 and 0 174 448. Bischoff E, Schirmacher W: Allergologie 1984; 7: 446–9; 1985; 8: 36–8; Bischoff E. Schirmacher W, Schober G: Allergologie 1985; 8: 97–9. Bronswijk JEMH van, Bischoff E, Schirmacher W, Berrens L, Schober G, J Med Entomol 1986; 23: 217–8). However, the results obtained do not really provide data of relevance to the desired estimation of the environmental allergenic load associated with manifest allergic disease. The nitrogenous waste product guanine produced by arthropods, spiders, insects, birds and some mammals has shown to be a highly insoluble low-molecular weight organic compound totally devoid of any detectable allergenic activity. The measurement of its contribution to the dry weight of house dust samples can therefore be no more than an approximate index of the total biomass of organisms contributing to the overall pool of components in house dust, whether allergenic or not. Results obtained in this fashion can, therefore, not be extrapolated or converted into any realistic parameter for the environmental content of biologically active allergenic macromolecules deriving from a great many potentially allergenic substrates. In accordance, investigations into the relationship between guanine content of house dust samples and immunological parameters for true allergen content have shown only crude statistical approximations of the presumed past and present population of mites in the dust samples {Bronswijk JEMH van. Exp Appl Acarology 1986; 2: 231–8.; Bronswijk JEMH van, Reumer JWF, Pickard R. Exp Appl Acarology 1987; 3: 271–8.; Pauli G, Hoyet C, Tenabene A, Le Mao J, Thierry R, Bessot JC. Clin Allergy 1988; 18: 383–92}. The availability of a method for the estimation of the total or specific allergen content of environmental dust samples based on the measurement of biologically really relevant allergenic properties and not on biologically inert and accidental by-products would be desirable.

In contrast to the commonly accepted structural theory of allergy, whereby allergenic macromolecules are recognized as antigens by specific (IgE-) antibodies, it has been proposed that allergens may by themselves be biologically active molecules, exerting their action in atopic people by an intrinsic molecular property that distinguishes them from all other antigens (Berrens L. Ann Allergy 1976; 36: 351–61). For the deployment of this inherent biological activity in allergic subjects no antibodies of any class have been considered essential. In this connection, it has for example been demonstrated that the collection of allergens in house dust exerts the function of activating the so-called complement system of zymogens in human beings without the detectable participation of antibodies {Berrens L. Guikers CLH. Van Rijswijk-Verbeek J. Immunochemistry 1976; 13: 367–72).

According to the present invention it was found that major allergens are proteolytic enzymes. This is totally unexpected in view of the scientific literature on possible enzymes in house dust or dust mite extracts proved highly discouraging (Bousquet J. Hale R. Guerin B. Michel F-B. Ann Allergy 1980; 45: 316–21; Stewart GA. Butcher A. Lees K. Ackland J. J Allergy Clin Immunol 1986; 77: 14–24): no enzymes even remotely capable of initiating enzyme cascades were detected.

SUMMARY OF THE INVENTION

Accordingly the present invention relates to the use of enzymatic properties of allergens, in particular the proteolytic property to hydrolyse amide and/or ester linkages.

Embodiments of the present invention comprise the use based on the intrinsic protease property of allergens from mammalian and non-mammalian excrement sources of animals such as arthropods, insects, birds and mammals to hydrolyse proteins and split substrates specific for the enzyme active sites;

the use based on the intrinsic property of allergens from mammals and present in the saliva, sweat, dry skin scales, and urine, of acting as glandulary kallikrein enzymes capable of splitting low-molecular weight substrates specific for tissue kallikreins.

According to the present invention it appears that house dust extracts not only contain powerful proteolytic enzymes, but that the enzymatic activities measured by employing active site-specific substrates correlate strongly with the IgE-binding capacities of such extracts. Major allergens from individual substrates like Dermatophagoides mites, from insects like locusts, cockroaches, the common housefly, the bug *Trogoderma angustum* etc., and from the dry dusty excreta of birds and other animals in fact are identical to—or intimately associated with—digestive proteolytic enzymes (i.e serine proteases with the specificities of trypsin and chymotrypsin) released into the environment by expulsion from the alimentary tracts.

Allergens associated with the secreta in the sweat (or in horny layer skin flakes), saliva and urine of animals like cats, dogs, mice, rats, horses and other mammals are actually identical to the respective tissue kallikrein enzymes secreted with these body fluids. These (glandulary) kallikrein enzymes exhibit a substrate specificity slightly different from that of trypsin-like serine proteases deposited with the excreta.

The intrinsic biological property of enzymatic action opens a complete range of techniques. An important example is the rapid, easily accessible, and inexpensive assay of the total and specific allergenic potential of the environment in people's homes or elsewise. Protease activity measured by means of quantitative test systems based on the present invention permits the graded evaluation of the contribution to the allergenic potential in dust samples by the biomass deriving from animal and plant sources.

One of the most aggressive allergens accumulating in the dust of human dwellings originates from mites of the *Dermatophagoides* species. It has been recognized that "interpretation of the relationship between allergic symptoms and mite-allergen exposure will require measurement of mite-allergen levels in individual houses" (Platts-Mills TAE, Hayden ML, Chapman MD, Wilkins SR. J Allergy Clin Immunol 1987: 79: 781–91). Two major allergens from this source are known, viz: an allergen P1 (Der p I) mainly associated with the mite excreta, and an allergen DPX (Der p II) mainly associated with (clean) whole mite bodies. During our isolation studies of the allergen P1 from mite cultures applicant has found that this allergen is identical to the protease described in this invention, so that measurement of the proteolytic or amidolytic activity of mite culture extracts provides an accurate assessment of the P1-content.

According to the present invention allergenic macromolecules in environmental dust samples and deriving from insect or animal sources can be detected and estimated quantitatively by measuring the protease activity of aqueous extracts towards different specific substrates. Because of the close correlation between the IgE-binding properties of such extracts from the serum of specifically allergic human subjects on the one hand, and the specific and quantitative protease potency of the extracts on the other, the proposed techniques and quantitative assay systems are also directly applicable for the (pharmaceutical) validation and standardization of allergenic extracts intended for use in man as diagnostic or therapeutic agents. The technological configuration of the pertinent test kits permits the reliable and quantitative evaluation of the allergenic contribution by proteolytic enzymes from plant sources as well, particularly from pollen, yeasts and moulds.

In the case of the use of the proteolytic (or amidolytic or esterolytic) activity according to the present invention it is observed that all types of substrates containing amide and/or ester linkages are suited, e.g. proteins or other peptide derivatives comprising an amino acid or amino acid sequence designed to fit the active site of proteases with the substrate-specificity of human and bovine trypsin and chymotrypsin.

In the case of kallikrein enzyme activity similar compounds having the substrate specificity of animal glandulary kallikreins are suited. Examples of peptide derivatives are the naphthylamides of monoamino, dipeptide, tripeptide or oligopeptide compounds or alkylesters of naphtyl, p-benzoyl or p-tosyl chromogenic conjugates of monoamino, dipeptide, tripeptide or oligopeptide derivatives comprising an amino acid or amino acid sequence designed to fit the active site of proteases with the substrate-specificity of human and bovine trypsin and chymotrypsin or with the substrate-specificity of animal glandulary kallikreins, respectively.

The present invention also relates to all possible test systems such as kits for the use of the enzymatic properties of allergens as described in the above. An average expert will be able to design a suitable kit on the basis of the above description. Preferably, a test system according to the invention comprises at least a carrier containing a substrate of the type as defined in the above.

For example, the kits are composed of polystyrene microtiter strips which may or may not be precoated with chromogenic or fluorogenic substrates and required for the determination of proteolytic, amidolytic or esterolytic activity, as well as animal glandulary kallikrein activity. These analytical systems may be extended with substrates for the assay of other enzymes or enzyme-inhibitors with relevance to human hypersensitivity disease in the broadest sense. The substrates may also be enclosed in the kits in buffered solution or in the form of lyophilized preparations. The results with extracts of environmental allergens may be evaluated quantitatively by reading optical densities or measuring fluorescence output in any of the current laboratory equipment available for spectrophotometry, fluorimetry or standard Enzyme Immuno Assays. The kits may be supplemented with multichambered plastic syringes featuring a separate compartment for introducing the dry dust sample to be examined, connected to a chamber containing the extracting fluid separated by way of a punch-through membrane. The present invention also comprises kits containing the substrates and buffer solutions only, in order to carry out enzymatic analysis in tubes or optical cuvettes, or containing ready-to-use fibrin plates in plastic dishes for estimating the fibrinolytic potential of environmental dust extracts and experimental or commercial allergenic preparations.

The present invention also relates to isolation methods of allergens from animal or botanical sources based on their properties as proteases.

One of the most powerful allergens accumulating in the dust of human dwellings originates from mites of the *Dermatophagoides* species. Two major allergens from this source have been identified, viz: an allergen P1 (Der p I) mainly associated with the mite excreta, and an allergen DPX (Der p II) mainly associated with (clean) whole mite bodies. (Chapman M. D., Platts-mills TAE. Clin exp Immunol 1978; 34: 126–36; J Immunol 1980; 125: 587–92).

Human respiratory allergy to cats is a widely known example of animal allergy in human (atopic) subjects. The most important allergens causing the specific symptoms are known to be associated with the animal's emanations as represented by the (dried) particles of the secreta sweat (skin, dander, fur), saliva, and urine. Extensive studies on the chemical nature of the allergen have remained restricted to the skin-associated antigen, which has been isolated and characterized as "Cat Allergen 1", or Fel d 1 (Ohman, J. L., Lowell, F. C., Bloch, K. J., J Allergy Clin Immunol 1973; 52: 231–41; Leitermann, K., Ohman, J. L., J Allergy Clin Immunol 1984; 74: 147–53).

The methods described in the above-mentioned references can be summarized by the following steps:
extraction of raw material to obtain an extract;
dialysis of said extract to obtain a retentate; and
chromatography of said retentate.

However, these techniques do not make use of the specific protease properties of these allergens, and the isolated products may have become inactivated and thus not be representative of the natural allergens.

The present invention relates to allergens from the digestive tract and the glandulary excreta of animals or from botanical sources as compounds substantially identical to or closely related to enzymes.

By means of the allergens according to the invention the purification, isolation and standardization process can be guided by means of highly specific, fast and inexpensive enzymatic techniques.

An embodiment of the present invention comprises major allergens from the digestive tracts of mammalian and non-mammalian organisms, which occur in the excreta and cause immunologically specific hypersensitivity reactions in atopic human beings, as compounds identical to, or intimately associated with proteolytic enzymes having the molecular characteristics of (bovine) trypsin and chymotrypsin.

A further embodiment of the present invention comprises major allergens from the digestive tracts of mammalian and non-mammalian organisms and occurring in their secreted saliva, urine, sweat, in their skin or skin-exfoliations, and which cause immunologically specific hypersensitivity reactions in atopic human beings, as compounds identical to, or intimately associated with the kallikrein (kininogenase) enzymes in these secretions.

The physicochemical properties of the isolated trypsin- or kallikrein-like enzymes are wholly compatible with the published data for individual allergens isolated by way of the traditional skin-testing or IgE-binding techniques, indicating that the suspected particular properties of atopic allergens that "distinguish them from other antigens" may in fact be those of proteolytic enzymes, e.g. molecular size range and isoelectric points (Berrens, L., The Chemistry of Atopic Allergens, Karger AG, Basel 1971).

The invention further relates to a method for isolating allergens from animal or botanical sources which is based on the affinity-binding to reversible enzyme (i.e. protease) inhibiting substances.

DETAILED DESCRIPTION OF THE INVENTION

Figure 1:
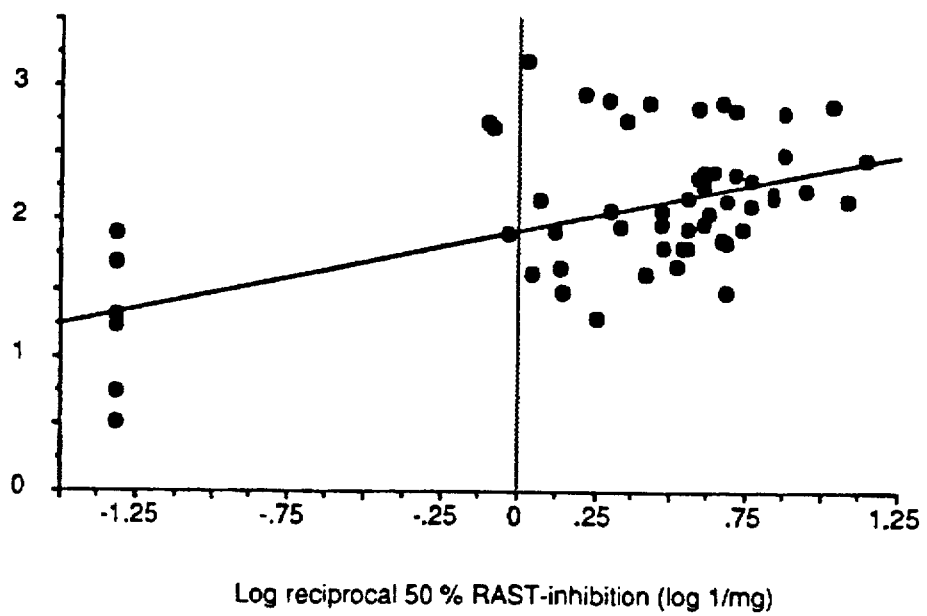

The method according to the present invention comprises in particular the steps of extraction of animal or botanical raw material to obtain an extract;

dialysis of said extract to obtain a retentate; and affinity chromatography of said retentate using a chromatographic support containing a protease inhibitor.

Preferably, all the steps of the method according to the present invention are carried out at a temperature at which no deterioration of the protease properties of the allergens occur. In general, the temperature during the extraction and dialysis will be in the range of 0° C. to about 30° C. On the one hand a relatively high temperature is required for an optimum extraction of the allergens, on the other hand one will try to avoid thermal denaturation. Normally, one will work at ambient temperature. The step of the affinity chromatography (as one possible way to obtain the end product) will be carried out at a lower temperature, e.g. 0°–10° C., preferably 0°–4° C.

General procedures for extraction and dialysis in the method according to the present invention may be as follows:

The crude source material containing the allergenic enzyme(s) is dispersed in a neutral buffer solution of 0.01–0.1M concentration containing a minimum of 0.001% of a suitable antibacterial agent like sodium azide, and between 0.1–0.5% of a water-miscible nonionic detergent of the Tween® series. Suitable buffers are adjusted to a pH-value between pH 7–8 for extraction and may consist of the sodium salts of phosphates, borates, barbiturates or any other anion dependent on the nature of the source material. The dispersion is stirred for at least 1 hour, whereby the temperature must not exceed 10° C. The mixture is then centrifuged, the supernatant stored between 4°–10° C., and the residue re-extracted for a period between 1–18 hours at 4°–10° C. with stirring. After recentrifugation, the residue is discarded and the combined supernatant extracts are dialysed for a period of 4–18 hours against distilled water from commercially available dialysis membranes with an exclusion limit of 10 000 daltons molecular size. The material inside the dialysis bags after this period (or "retentate") is dried by lyophilization to provide the starting material for further purification of the allergenic enzyme by salt fractionation, affinity chromatography or elsewise. Alternatively, the dialysis may be carried out by passage of the extract through columns filled with molecular sieving materials like Sephadex® or Sephacryl® of the exclusion types G10/G25 or the corresponding S-sizes. The material in the fluid of the non-retained breakthrough effluent is then dried by lyophilization to provide the starting material for further purification of the allergenic enzyme.

The proteolytic enzyme properties of major allergens according to this invention may be used for their rapid concentration and isolation from aqueous solutions by affinity chromatography on columns carrying conjugated (reversible) protease inhibitors for the allergen under consideration. Examples of suitable carrier supports for covalent coupling to the inhibitor with the aid of a bifunctional coupling agent are: cellulose or partially substituted cellulose derivatives, among which those of the Sephadex® and Sepharose® series, and other insoluble (hei-)cellulose or natural polysaccharides like agar or agarose. Examples of suitable enzyme inhibitors for immobilization are the polyvalent bovine inhibitor BPTI (Trasylol®), soybean trypsin inhibitor (SBTI), the lima bean inhibitor LBTI, the trypsin and kallikrein inhibitors from hen's eggwhite (ovomucoid and other ovo-inhibitors), the protease inhibitors from potatoes, peanuts, and other botanical sources, and from the snail Helix pomatia. Examples of suitable synthetic inhibitors are benzamidine (as demonstrated in Example IX) and the compounds 4-aminomethylbenzamidine and 4-amidinphenylpyruvic acid.

During the extraction, isolation and purification procedures as outlined, denaturation of the enzyme may occur, causing a diminution of the measurable catalytic properties; this does not decrease the value of the allergen as a diagnostic or therapeutic agent, because it will retain its antigenic properties and be detectable as such by immunological or clinical methods.

EXAMPLE I

In a preliminary screening experiment, 11 dust samples were examined for the relationship between RAST-inhibitory power and enzyme activity towards the tripeptide chromogenic substrate H-D-Isoleucyl-L-prolyl-L-arginine-p-nitroanalide-di HCl, (=I.P.A.). Samples of dry dust were collected by vacuum-cleaning from individual houses in The Netherlands. Extracts were made by weighing exactly 1 gram of the dust sample and extracting overnight with 5 ml of buffer at +4° C. on a roller bank. The buffer used for the extraction and the preparation of the dilutions consisted of 1 part phosphate buffer 0.1M, pH 7.4 and 9 parts of 0.9% NaCl in distilled water, and the solution was brought to contain 0.01% sodium azide and 0.5% of the detergent Tween-20. After centrifugation, the clear supernatant was stored frozen at −20° C. Before the analyses, the samples were thawed at room temperature and recentrifuged, whereupon aliquot samples of extract were carefully pipetted from the supernatant fluids.

For Radio Allergo Sorbent Test (RAST)-inhibition, 50 µl aliquots of pooled human, mite-RAST positive serum (diluted 1:5.5) were mixed in plastic round-bottom tubes with serial dilutions of the extracts to a total end volume of 100 µl. The mixtures were incubated for 1 hour at room temperature and subsequently left overnight at +4° C. To each tube, a 5 mm diameter paper disc was then added which had been coupled by means of cyanogen bromide to whole extract of a culture of the house dust mite *Dermatophagoides pteronyssinus* (discs obtained commercially from Pharmacia AB, Uppsala, Sweden, code d1, batch nr. 7784). After 3 hours incubation at room temperature and a subsequent washing step, IgE-antibodies fixed from the serum sample onto the discs was measured by incubation with radioactive anti IgE purchased from Pharmacia AB, Uppsala, Sweden. After a further washing step, the radioactivity bound firmly to the discs was finally evaluated in a Gamma-Counter. Graphs were plotted of the house dust extract dilutions against the percentage of radioactivity in the test system bound to the discs, from which the dilution causing 50% inhibition of IgE-binding was found by interpolation. Values were recalculated per ml of extract of the original dry dust sample causing 50% RAST-inhibition, corrected for a specific reagent binding.

In the extracts of these samples the proteolytic enzyme activity was assayed by pipetting 300 µl of the extract, together with 600 µl Tris(hydroxymethyl)aminomethane (TRIS)-HCl buffer (0.1M, pH 8.4) and 25 µl of a solution of the synthetic chromogenic tripeptide substrate H-D-Isoleucyl-L-prolyl-L-arginine-p-nitroanilide-di-HCl, (=I.P.A.) into quartz cuvettes of 0.1 cm light path fitted into the thermostatted (37° C.) holder of a recording spectrophotometer. The enzymatic conversion of the substrate was followed by reaction rate analysis, whereby the optical density (E) at 405 nm of the liberated p-nitroaniline (pNA) reaction product was recorded per minute. The increment of optical density in the linear portion of the velocity curve in the 3rd minute was read as $\Delta E$ from the rate record and taken as a basis for calculation of the enzymatic potency; for the very dark coloured extracts a blank was taken, containing 100 µl of extract in the blank (no substrate) whereby the enzymatic activity was evaluated from the reaction rate in the 1st minute. The results were expressed in mU/ml of extract, i.e. mU/0.2 g of original dry dust by applying a conversion factor of 210. The comparative data are shown in Table A.

Table A. Results of analysis by RAST-inhibition and enzyme activity on tripeptide chromogenic substrate I.P.A. in extracts of 11 different samples of house dust collected in The Netherlands.

TABLE A

| dust sample | $\Delta E$ in 3rd min | mU/ml | mg dust for 50% RAST-inhibition |
|---|---|---|---|
| A | 0.040 | 8.4 | >20 |
| B | 0.035 | 7.3 | 5.9 |
| C | 0.040 | 8.4 | 29 |
| D | 0.020 | 4.2 | >20 |
| E | 0.007 | 1.5 | >>20 |
| F | 0.017 | 3.6 | 5.5 |
| G | 0.005 | 1.0 | >>20 |
| H | 0.006 | 1.3 | >20 |
| I | 0.075 | 15.7 | 1.1 |
| J | 0.245 | 51.1 | 1.3 |
| K | 0.000 | 0.0 | 0.0 |

Composition of the Reagents

TRIS-buffer: 12.1 g Tris(hydroxymethyl)aminomethane and 6.2 g NaCl are dissolved in 800 ml dist.$H_2O$; the solution is brought to pH 8.4 by dropwise addition of 1N HCl and then adjusted to exactly 1000 ml.

H-D-Isoleucyl-L-prolyl-L-arginine-p-nitroanilide-di HCl, (=I.P.A.), specific for trypsin-like serine proteases, Mol. wt.=577.6, 25 mg lyophilized product dissolved in 7.2 ml distilled water (1.5 µMole/ml). The solution is stable for 2 months at +4° C.

Calculation

A calculation factor was computed of $(313\times0.2)/1000= 0.0626$. The extinction increment $\Delta E$ in the 3rd min was read from the record and the result in mU per quantity of dry allergenic material in the test solution was calculated as $\Delta E\times1000\times0.0626$. Finally, the number of mU per mg of allergenic material was calculated.

Evaluation

From these preliminary data a graph was constructed, which indicated for this limited number of samples a good correlation between the parameters, i.e. a positive correlation between the RAST-inhibitory power of the dust sample extracts and the esterolytic activity towards the specific I.P.A. chromogenic serine protease substrate (linear regression line $y=1.18\times0.44$; $r=0.74$).

EXAMPLE II

Samples of dry dust were collected by vacuum-cleaning from 74 individual houses in The Netherlands. Extracts were made by weighing exactly 1 gram of the dust sample and extracting overnight with 5 ml of buffer at $+4°$ C. on a roller bank. The buffer used for the extraction and for the preparation of the dilutions consisted of 1 part phosphate buffer 0.1M, pH 7.4 and 9 parts of 0.9% NaCl in distilled water; the solution is brought to contain 0.01% sodium azide and 0.5% of the detergent Tween-20. After centrifugation, the clear supernatant was stored frozen at $-20°$ C. Before the analyses, the samples were thawed at room temperature and recentrifuged, whereupon aliquot samples of extract were carefully pipetted from the supernatant fluids.

For Radio Allergo Sorbent Test (RAST)-inhibition and assay of the proteolytic enzyme activity on the synthetic chromogenic tripeptide substrate I.P.A. The same procedures were followed as described under EXAMPLE I. In addition, the following assay kit was used for evaluating the enzymatic activity of the extracts versus the chromogenic tripeptide substrate H-DValyl-L-leucyl-L-arginine-p-nitroanilide-di HCl (=V.L.A., Mol. wt=579.6; 25 mg dissolved in 28.8 ml dist. water=1.5 μMole/ml). For this assay of kallikrein activity 50 μl of allergenic extract solution (1 mg/ml) was pipetted into the wells of a polystyrene microtiter strip, together with 140 μl TRIS-HCl buffer pH 8.2 and 10 μl V.L.A.-solution. The strips were stored in an incubator for 30 min at $37°$ C., whereupon the reaction was stopped by the addition of 50 μl 50% acetic acid. The optical densities in each well were then read at 410 nm in a Micro-strip ELISA Reading Equipment relative to the appropriate controls. The assays were performed in duplicate.

The combined analytical data have been listed in Table B. In all assays, a control was included for 50 μl without substrate but with buffer instead to correct for the (often pronounced) background colour of the extract itself.

Table B. Results of RAST-inhibition, protease (I.P.A., V.L.A.) and acid phosphatase (A.P.) assay in 74 dust samples.

TABLE B

| Sample nr. | mg dry dust for 50% RAST-inh. | I.P.A. mU/ml *) | V.L.A. $E_{410\,nm}$ |
|---|---|---|---|
| 1 | 0.54 | 18 (0.09) | 0.26 |
| 2 | 0.22 | 220 (0.69) | 0.30 |
| 3 | 0.36 | 701 (0.96) | 0.31 |
| 4 | 0.20 | 67 (0.28) | 0.32 |
| 5 | 0.27 | 80 (0.32) | 0.28 |
| 6 | 0.19 | 203 (0.70) | 0.32 |
| 7 | 0.20 | 29 | 0.29 |
| 8 | 0.14 | 150 | 0.31 |
| 9 | 1.21 | 501 (1.02) | 0.34 |
| 10 | 0.37 | 39 | 0.29 |
| 11 | 0.69 | 28 | 0.26 |
| 12 | 0.14 | 150 (0.63) | 0.35 |
| 13 | 0.23 | 108 | 0.29 |
| 14 | 0.24 | 91 | 0.33 |
| 15 | 0.45 | 86 | |
| 16 | 0.83 | 134 | 0.31 |
| 17 | 0.74 | 78 | 0.28 |
| 18 | 0.29 | 44 | 0.34 |
| 19 | 0.24 | 169 | |
| 20 | 1.18 | 451 | 0.33 |
| 21 | 0.24 | 190 | 0.31 |
| 22 | 0.11 | 160 | 0.33 |
| 23 | 0.24 | 213 | 0.32 |
| 24 | 0.20 | 131 | 0.31 |
| 25 | 0.21 | 720 (1.20) | 0.32 |
| 26 | 0.07 | 265 | 0.30 |
| 27 | 0.18 | 81 | 0.29 |
| 28 | 0.13 | 582 | 0.30 |
| 29 | 0.25 | 639 | 0.30 |
| 30 | 0.09 | 689 | |
| 31 | 0.43 | 526 | 0.32 |
| 32 | 0.13 | 295 | 0.33 |
| 33 | 0.21 | 68 | 0.30 |
| 34 | 0.19 | 626 | |
| 35 | 0.17 | 119 | 0.30 |
| 36 | 0.32 | 59 | 0.30 |
| 37 | 0.27 | 59 | 0.30 |
| 38 | 0.17 | 188 | 0.30 |
| 39 | 0.91 | 1440 (1.27) | 0.24 |
| 40 | 1.43 | 6 | |
| 41 | 0.38 | 41 | |
| 42 | 4.35 | 19 | |
| 43 | 0.17 | 63 | |
| 44 | 1.05 | 48 | |
| 45 | 0.27 | 0 | |
| 46 | 0.42 | 0 | |
| 47 | 2.00 | 0 | |
| 48 | 1.67 | 0 | |
| 49 | 0.49 | 110 | |
| 50 | 0.33 | 113 | |
| 51 | 1.05 | 75 | |
| 52 | 0.59 | 801 | |
| 53 | 6.67 | 38 | |
| 54 | 0.77 | 0 | |
| 55 | 0.21 | 0 | |
| 56 | 0.26 | 9 | |
| 57 | 0.87 | 39 | |
| 58 | >20 | 46 | |
| 59 | >20 | | |
| 60 | >20 | 19 | |
| 61 | >20 | 3 (0.02) | .016 |
| 62 | >20 | 74 | 0.29 |
| 63 | >20 | 5 | 0.32 |
| 64 | >5 | | |
| 65 | >20 | 18 | 0.31 |
| 66 | >20 | 16 | 0.31 |
| 67 | 0.08 | 132 | |
| 68 | 0.25 | 200 | 0.32 |
| 69 | 0.27 | 140 | |
| 70 | 0.14 | 138 | |
| 71 | 0.71 | 43 | 0.29 |
| 72 | 0.28 | 60 | 0.30 |
| 73 | 0.33 | 90 | 0.27 |
| 74 | 0.50 | 751 | |

*Test system in tubes; values between brackets were determined in microtiter plate design: 50 μl of sample (= 50 μg), 140 μl Tris-HCl buffer pH 8.3. 10 μl substrate incubated for 5 minutes at $37°$ C.; the reaction with I.P.A. is very fast under these conditions.

The results for the RAST-inhibition versus I.P.A. activity are shown in FIG. 1, together with the linear regression line and the coefficient of correlation. The Spearman rank correlation coefficient was 0.421 (N=59, P<0.01).

Thus, there is a significant correlation between the RAST-inhibitory power and the (trypsin-like) amidolytic activity extractable from the dust samples: the higher the enzyme activity on I.P.A., the less material is needed for 50% RAST-inhibition, meaning that the enzyme activity and the IgE-binding allergens are positively correlated. This correlation is much better than between the mite count and RAST-inhibition or between RAST-inhibition and guanine content established in the same samples (Bronswijk JEMH van, Reumer JWF, Pickard R. Exp Appl Acarology 1987; 3: 271–8).

The correlation coefficient between log 50% RAST-inhibition and the enzymatic activity on the substrate V.L.A. was only 0.35 (0.01<P<0.025), indicating that the allergenic enzymes in house dust are trypsin-like and largely derive from insect or arthropod (mite) excreta.

EXAMPLE III

The chromogenic tripeptide substrates for serine esterases employed in the EXAMPLES I and II are the reagents to be preferred in test kits, because they are quite stable, both in buffered solution and in the dry state. However, more simple and economic substrates may also be used, for example the compound N-α-Benzoyl-DL-arginine-p-nitroanilide. HCl (BAPNA, M=434.89), which similarly produces p-nitroaniline pNA on enzymatic hydrolysis by trypsin-like proteases. Its major disadvantage, however, is a lesser stability and shelf life than I.P.A., necessitating the daily preparation of fresh solutions from the dry product. The BAPNA used in the experiments recorded in EXAMPLE III was purchased from British Drug Houses Inc. (BDH), Poole (Great Britain).

A suitable microtiter assay technique with BAPNA was developed using (per well in a polystyrene microtiter strip) 50 µl allergen solution (at 1 mg lyophilized nondialyzable extract per ml) in TRIS-HCl buffer (or a dilution series of bovine trypsin 50 µg/ml in 0.001N NaOH), 100 µl 0.1M TRIS-HCL buffer pH 8.3 containing 0.01M $CaCl_2$, 60 µl BAPNA solution (20 mg/460 µl dimethylsulfoxide (DMSO); dilute 1:100 in TRIS-buffer). The strips were covered with a Parafilm® sheet and incubated for 30 min at 37° C. The reaction was terminated by adding 40 µl 50% acetic acid to each well and the optical densities were finally read in an ELISA-Reader at 410 nm. The activities of the allergenic preparations were expressed in equivalents trypsin by intrapolation on a calibration curve made with crystalline bovine trypsin and BAPNA.

A comparative trial experiment on 10 dust samples, listed in Table C shows that the results with the two substrates I.P.A. and BAPNA are indeed well correlated (Spearman rank coefficient of correlation r=0.852, 0.0001<P<0.005), so that both are suited for the purpose of assessing the allergenic activity of house dust extracts.

Table C. Results of RAST-inhibition, I.P.A. and BAPNA assay in microtiter strips in 10 extracts of different dust samples.

TABLE C

| Sample nr. | RAST-inhibition, mg dry sample for 50% -inh | I.P.A. nU/ml | BAPNA in µg trypsin/50 µl |
|---|---|---|---|
| 1 | 0.54 | 18 | 0.225 |
| 2 | 0.22 | 220 | 0.450 |
| 3 | 0.36 | 701 | 0.575 |
| 4 | 0.20 | 67 | 0.500 |
| 5 | 0.27 | 80 | 0.350 |
| 6 | 0.19 | 203 | 0.450 |
| 9 | 1.21 | 501 | 0.950 |
| 12 | 0.14 | 150 | 0.450 |
| 25 | 0.21 | 720 | 1.150 |
| 39 | 0.91 | 1440 | 1.150 |

Other Possible Substrates

In the course of these investigations, a number of other compounds was examined for application as substrates for serine esterases relevant for allergenic activity. These concerned:

N-α-Benzoyl-L-arginine ethylester. HCl (BAEe), which produces ethanol and $H^+$-ions on hydrolysis. This compound proved highly valuable for measuring the enzymatic activity of dust extracts by means of a pH-stat assay, producing results well correlated with the colorimetric I.P.A. and BAPNA assays shown in EXAMPLES II and III; however, the substrate is quite unstable in solution.

N-α-Benzoyl-DL-arginine-β-naphthylamide. HCl (BANA), a chromogenic substrate for enzymes with trypsin specificity. The compound produces β-naphthylamine on hydrolysis, which may subsequently be diazotized with a Fast stain to give a visually coloured (red or blue) reaction product.

H-D-Valyl-Leucyl-Lysine-p-nitroanilide. 2 HCl (V.L.L., M=551.5) which has a slightly different (plasmin) specificity from I.P.A. and V.L.A. The hydrolysis of this substrate by enzymes in pollen extracts is shown in EXAMPLE IV.

p-Tosyl-L-Arginine Methylester (TAMe), a specific substrate for chymotrypsin-like enzymes in dust samples. Enzymatic hydrolysis produces methanol and $H^+$ ions; the methanol released may be assayed colorimetrically with chromotropic acid and concentrated $H_2SO_4$. Alternatively, the released $H^+$ ions may be measured in a kinetic pH-stat assay. This product is unstable, a solution having a shelf life of one day.

synthetic(tri-peptide 4-methylcoumarin (or -umbelliferone) amides as fluorogenic substrates for measuring enzymatic split products by fluorescence output.

The naphthylamide- and nitroanilide chromogenic substrates, but not the BAEe or TAMe esters are hydrolysed enzymatically to yield reaction products which may with relative ease be converted into red or blue coloured pigments by diazotation. Hence, instead of monitoring the reaction colorimetrically, it is also possible to allow the enzymatic conversion to proceed in or on a solid (starch or cellulose) support to be presented as semi-quantitative test "dip"-sticks. Furthermore, these chromogenic tripeptides are quite suitable for use in automated analytical assay systems.

EXAMPLE IV

Table D. Specific protease enzymatic activities per mg of lyophilized nondialyzable allergenic components from the pollen of grasses, trees, weeds and shrubs, as examples of allergen control and-standardization.

TABLE D

| Species | V.L.A. mU/mg |
| --- | --- |
| Acer negundo | 8.4 |
| Agrostis alba | 2.0 |
| Alnus tenuifolia | 1.4 |
| Ambrosia elatior | 5.2 |
| Anthoxanthum odoratum | 4.9 |
| Arrhenaterum elatius | 2.4 |
| Artemisia vulgaris | 5.6 |
| Avena sativa | 3.8 |
| Betula populifolia (alba) | 3.5 |
| Brassica napus | 7.0 |
| Chenopodium album | 1.4 |
| Chrysanthemum leucanthemum | 3.5 |
| Corylus americana | 1.2 |
| Cynodon dactylon | 4.4 |
| Dactylis glomerata | 8.4 |
| Fagus americana | 8.9 |
| Festuca elatior | 2.5 |
| Fraxinus pennsylvanica | 2.8 |
| Holcus lanatus | 1.2 |
| Juniperus monosperma | 1.2 |
| Lolium perenne | 3.7 |
| Olea europea | 3.0 |
| Parietaria officinalis | 3.4 |
| Phleum pratense | 5.1 |
| Plantago lanceolata | 2.8 |
| Poa pratensis | 16.1 |
| Populus deltoides | 2.1 |
| Quercus rubra | 29.7 |
| Rumex acetosella | 0.0 |
| Salix-discolor | 5.2 |
| Secale cereale | 3.3 |
| Solidago spp. | 1.8 |
| Taraxacum officinalis | 5.2 |
| Triticum sativum | 1.8 |
| Ulmus americana | 15.0 |
| Urtica dioica | 5.9 |
| Zea mays | 0.4 |

Pollen preparations also split the synthetic peptide substrate H-D-Valyl-Leucyl-Lysine-p-nitroanilide, 2 HCl (V.L.L.) for the fibrinolytic protease plasmin, although at a very slow rate. In a series of experiments, 200 µl samples of pollen preparations dissolved in 200 µl TRIS-HCl buffer (0.05M pH 8.3, containing 0.01% w/v Tween-20) were pipetted into microtiter plate flat-bottom wells, and 15 µl V.L.L. (1.5 µMole/ml) in the same buffer was added. The plates were covered with Parafilm® and kept at 37° C. for 2.5 hours. The reaction was then stopped by adding 25 µl 50% acetic acid and the optical density was evaluated at 410 nm in an ELISA-Reader. Some representative results have been listed in Table E.

Table E. Conversion of chromogenic tripeptide substrate V.L.L. by high-molecular weight non-dialysable pollen samples prepared from USA-I dry pollen. Results in O.D.-readings at 410 nm per 200 µg of preparation.

TABLE E

| Pollen preparation | O.D. 410 |
| --- | --- |
| Agrostis alba | 0.59 |
| Anthoxanthum odoratum | 0.93 |
| Betula populifolia | 0.76 |
| Cynodon dactylon | 0.60 |
| Dactylis glomerata | 1.59 |
| Festuca elatior | 0.90 |
| Holcus lanatus | 1.04 |
| Lolium perenne | 1.65 |
| Parietaria officinalis | 0.46 |
| Phleum pratense | 1.29 |
| Poa pratensis | 1.77 |

TABLE E-continued

| Pollen preparation | O.D. 410 |
| --- | --- |
| Olea europea | 0.50 |
| Secale cereale | 1.21 |

These data show that the common wind-borne pollen, especially from the Gramineae family exhibit (weak) plasmin activity, like other allergenic preparations (not presented here). This finding explains the fibrinolytic potency of allergenic preparations, as demonstrated in EXAMPLE VII.

EXAMPLE V

Table F. Enzymatic activity of highly allergenic materials form animal secreta and excreta, assayed on the highly purified major allergens or the total nondialysable lyophilized preparations HMWT with the glandulary kallikrein substrate V.L.A.

TABLE F

| Animal product | V.L.A. in mU/mg |
| --- | --- |
| Bee venum, pure | 0.3 |
| Cat dander HMWT, Preparation 1 | 7.7 |
| Cat dander HMWT, Preparation 2 | 0.6 |
| Cat dander Allergen 1, 1st batch (= Fel d I) | 4.1 |
| Cat dander Allergen 1, 2nd batch (= Fel d I) | 5.7 |
| Cat dander, Allergen 1-depleted | 0.9 |
| Cat urine, male | 30.0 |
| Cat urine, female | 20.0 |
| Cat urine, mixed sample | 15.7 |
| Cockroach, major allergen chromatographic fract. | 287.0 |
| Dog dander HMWT, Preparation 1 | 12.2 |
| Dog dander HMWT, Preparation 2 | 24.0 |
| Dog dander HMWT, Preparation 3 | 10.2 |
| Dog dander, Major Allergen 1, 1st batch | 44.0 |
| Dog dander, Allergen 1-depleted | 1.0 |
| Dog urine, male | 101.0 |
| Dog urine, female | 92.0 |
| Horse dander HMWT | 0.1 |
| Human dander, fraction C | 5.8 |
| Locust excreta, Preparation 1 | 1641.0 |
| Locust excreta, Preparation 2 | 1170.0 |
| Locust excreta, major allergen chromatographic fract. | 1299.0 |
| Musca domestica, clean body extract HMWT | 25.0 |
| Pigeon excreta, total HMWT preparation | 17.8 |
| Trogoderma angustum, HMWT preparation | 2235.0 |
| Wasp venom, pure | 4.0 |

These analyses show that the animal allergenic secreta exhibit appreciable (tissue) kallikrein activity, which coincides with the major allergens. The insect excreta are far more potent, even on V.L.A., because these are largely enzymes with trypsin- and chymotrypsin specificity which likewise split the V.L.A. tripeptide.

EXAMPLE VI

Table G. Enzymatic conversion of chromogenic tripeptide substrate V.L.A. by highly allergenic preparations from whole cultures or clean bodies of house dust mites of the *Dermatophagoides* species.

TABLE G

| Preparation | I.P.A., mU/mg |
|---|---|
| D.pteronyssinus WHO-Standard 82/518 | 152.0 |
| D.pteronyssinus NL,whole culture HMWT preparation 1 | 30.3 |
| D.pteronyssinus Allergen P1 (= Der p I), batch 1 | 157.0 |
| D.pteronyssinus Der p I - depleted, batch 1 | 2.3 |
| D.pteronyssinus NL,whole culture HMWT, preparation 2 | 50.3 |
| D.pteronyssinus Allergen P1 (= Der p I), batch | 296.4 |
| D.pteronyssinus Der p I - depleted, batch 2 | 3.2 |
| D.pteronyssinus NL, whole culture, preparation 3 | 73.3 |
| D.pteronyssinus, whole culture (U.K.) | 138.3 |
| D.pteronyssinus whole bodies (U.S.A.) (= Der p II) | 0.5 |
| D.farinae whole bodies (U.S.A.) (= Der f II) | 0.1 |

The enzyme activity of the mite preparations was also assayed with BAPNA and with I.P.A. for protease activity in a microtiter plate set-up as specified in Examples III and IV. The results are shown in Table H.

TABLE H

| MATERIAL | BAPNA E410 *) | BAPNP µg trypsin *) | I.P.A. E410 *) | A.P. E410 **) |
|---|---|---|---|---|
| D.pteron.whole culture (U.K.) | 0.19 | 0.400 | 1.10 | 1.30 |
| D.pteron. whole culture (NL) | 0.13 | 0.250 | 0.83 | 0.64 |
| P1-allergen, batch 1 | 0.24 | 0.500 | 1.03 | 1.00 |
| P1-depleted, batch 1 | 0.03 | <0.1 | 0.06 | 0.21 |
| D.pteronyssinus bodies (U.S.A.) | 0.02 | <0.1 | 0.00 | 1.23 |
| D.farinae bodies (U.S.A.) | 0.01 | <0.1 | 0.01 | 1.06 |

*) per 50 µg allergen preparation
**) per 20 µg of allergen preparation

These data confirm that the protease activity evidently is not associated with mite whole bodies but is excreted into the medium.

EXAMPLE VII

Fibrinolytic Activity

Test sets for quantitatively estimating the fibrinolytic activity of allergenic extracts were produced as follows. Human fibrinogen (KabiVitrum AB, Sweden, lot nr. 57024, 80 mg) was dissolved in 40 ml of distilled water; a mixture was also made of 1.6% agar (Difco Agar Noble) in VSB-gelatin buffer pH 7.8. The VSB-gelatin buffer consisted of 0.05M Veronal-Na, 0.1M NaCl and 0.25% gelatin (ionic strength µ=0.15) was made up by dissolving 10.3 grams of Veronal-Na, 5.84 grams of NaCl and 2.5 grams of gelatin in 1000 ml of bi-distilled water and brought to pH 7.8 by the dropwise addition of 1N HCl; 40 ml of this buffer was used for mixing with the fibrinogen solution after warming both solutions to 40° C. To 7 ml of this mixture was then added 200 µl of Test-Thrombin (20 IU/ml, Behringwerke ORHT, Germany, lot nr. 506003 D). The mixture was stirred on a Vortex mixer, poured into a Petri dish of 8.2 cm diameter and allowed to solidify. All solutions to be tested were made up at 10 mg/ml in a VSB$^{++}$-buffer pH 7.8. Aliquots of 10 µl of allergen solution (at 10 mg of lyophilized preparation per ml, except the WHO-D. pteronyssinus standard 82/518 which had a concentration of less than 1 mg/ml) were pipetted into holes punched in the fibrin-agar layer and the Petri dishes were allowed to stand at ambient temperature for 48 hours, or at 37° C. for 24 hours. The clearance diameter was then measured in mm under dark-field illumination and the result was squared. A standard curve was constructed with crystalline bovine trypsin (Sigma Chemical Corporation, U.S.A.) in the range of 25–200 ng trypsin per 10 µl per well. The results with the allergenic preparations were read on this curve and expressed in µg-equivalents of trypsin/mg allergen preparation.

Buffer Composition

VSB: Dissolve 41.5 g NaCl and 5.1 g veronal-Na (=sodium 5,5-diethylbarbiturate) in 750 ml distilled water. Bring to pH 7.35 with about 17 ml of 1N HCl and fill up to 1000 ml with dist. water.

VSB$^+$ : VSB to about 800 ml, add 5 ml of solution of 10.16 g MgCl$_2$, 6 H$_2$O (0.5M) and 2.46 g CaCl$_2$.2 H$_2$O or 1.665 g CaCl$_2$. 0 H$_2$O (0.15M) in 100 ml dist. water. Bring to 1000 ml with dist. water.

Both are stock solutions. For use, the stock is diluted 5× with distilled water to give the working solution of ionic strength µ=0.149.

The results obtained with some representative allergenic preparations have been listed in Table I. As expected, there was no correlation between the reactivity of some kallikrein-like allergens towards the tripeptide substrate V.L.A., and their fibrinolytic potency, which is essentially a trypsin-like specificity (unpaired t-test value–0.04, P>0.4).

Table I. Fibrinolytic activity of some important allergen preparations

TABLE I

| Allergen preparation | µg trypsin eq./mg |
|---|---|
| Cat urine HMWT, male | >>2.0 |
| Cat urine HMWT, female | >>2.0 |
| Cockroach culture, enzyme fraction | 0.68 |
| D. farinae whole body, U.S.A. | + |
| D.pteronyssinus whole body, U.S.A. | 0.0 |
| D.pteronyssinus WHO 82/518 | >>2.0 |
| D.pteronyssinus culture U.K. | >>2.0 |
| D.pteronyssinus whole culture NL | >>2.0 |
| D.pteronyssinus Allergen Der p I | >2.0 |
| D.pteronyssinus, Der p I depleted | 0.10 |
| Dog urine HMWT, male | 0.66 |
| Dog urine HMWT, female | 1.32 |
| Dog dander, HMWT product 1 | + |
| Dog dander, HMWT product 2 | 0.67 |
| Dog dander, Major Allergen 1 | 1.04 |
| Dog dander, Allergen 1 - depleted | + |
| Musca domestica, whole body | 1.0 |
| House dust, fraction E | 0.56 |
| Locust culture, enzyme fraction | >>2.0 |
| Pigeon excreta HMWT-product | 1.00 |

The most powerful fibrinolytic enzymes are consequently found among the excretion products contained in whole cultures of mites and insects, which are mainly trypsin-like enzymes to be measured with the I.P.A. chromogenic tripeptide substrate.

EXAMPLE VIII

Isolation of Trypsin-Like Enzyme from Cultures of Dermatophagoides pteronyssinus and Identity with the Major Allergen "Der p I".

1. Isolation of Major Allergen Der p I according to Chapman and Platts-Mills

D. pteronyssinus organisms were cultured on a mixture of washed human skin scales and dried yeast cells for about 3 months. After this period, the whole culture was heated for 30 min at 60° C. and powdered. The preparation was obtained commercially (HAL Laboratories, The Netherlands, batch nr. DP 801) and was extracted with stirring for 4 hours at 4° C. in phosphate-saline buffer, containing $10^{-3}$% sodium azide+0.5% Tween-20. The suspension was centrifuged and the residue was re-extracted overnight with the same extractant. The combined supernatants were dialysed for 4 hours against distilled water from Visking dialysis tubing (exclusion limit 10 000 daltons). The nondialyzable retentate portion HMWT was finally dried by lyophilization.

a. Gel filtration

Figure 2:
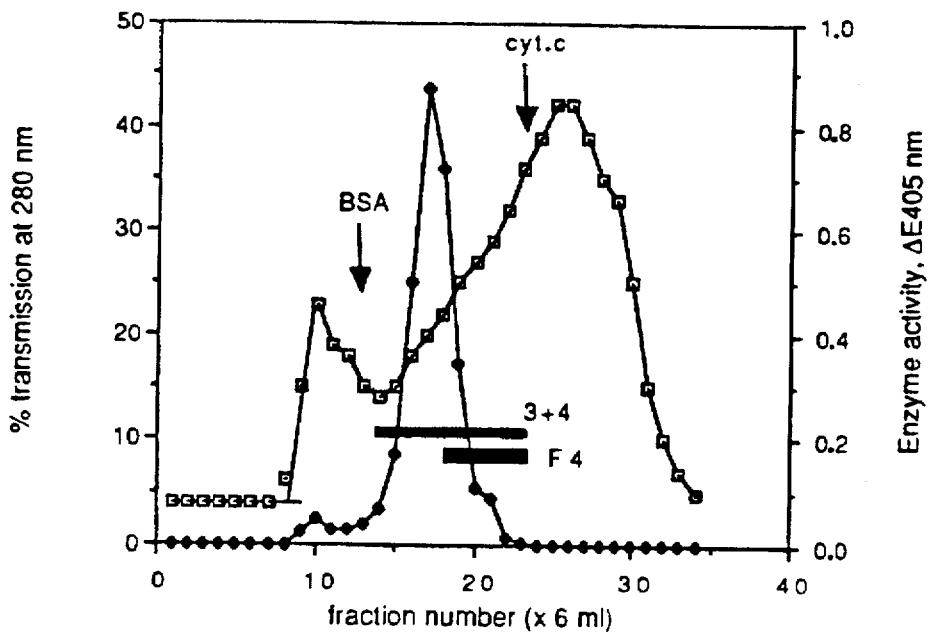
Figure 3:
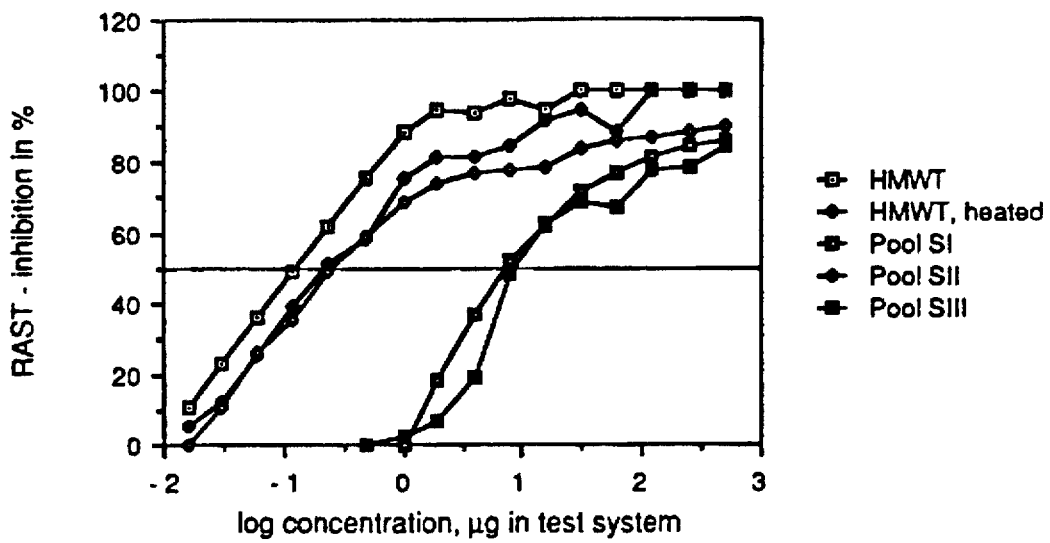

A chromatographic column was prepared of Sephadex G100 (90×1.6 cm) in borate-buffered saline (BBS, 0.01M borate buffer pH 8.0 in 0.9% NaCl).A solution of 25 mg HMWT in 1 ml BBS was applied to the top of the gel and the column was then percolated with the same buffer. Volumes of 6 ml were collected automatically with a fraction collector and the effluent was monitored continuously for UV-absorption at 280 nm as a parameter for protein content. The conversion of the chromogenic tripeptide substrate IPA was measured in tubes by taking 0.3 ml aliquots of each eluate fraction, adding 0.6 ml of buffer and 25 µl of substrate solution (=1.5 µMole/ml). The reaction was followed at 410 nm on a recording spectrophotometer and the increment in OD in the 3rd minute was taken for calculation. The position of the enzyme peak was established from a plot, shown in FIG. 2. On the guidance of this plot, 3 Pools were made as indicated in the legend to the Figure, which were dialysed against distilled water and lyophilized. Three runs were made, of 25 mg load on each run. The overall yields were: SI=44 mg, the enzyme peak SII=18 mg (24% in HMWT), SIII=14 mg, i.e. an overall recovery of 66%. RAST-inhibition experiments with serial dilutions of the starting HMWT-product and the three S-fractions were carried out on 50 µl samples of diluted human miteallergic blood serum using commercial mite allergen-coated discs and radioactive anti IgE-reagents according to the manufacturer's instructions (Pharmacia AB, Uppsala, Sweden). The results are shown in FIG. 3.

The ratios for 50% RAST-inhibition were

HMWT:SI:SII:SIII=0.13:7.94:0.25:7.94 in order of potency (reciprocals) 7.7:0.13:4.0:0.13 or 59:1:31:1

The ratios for amidolytic potency were

HMWT:SI:SII:SIII=128:16:438:18 or 8:1:27:1 b. Pevikon block electrophoresis

Figure 4:
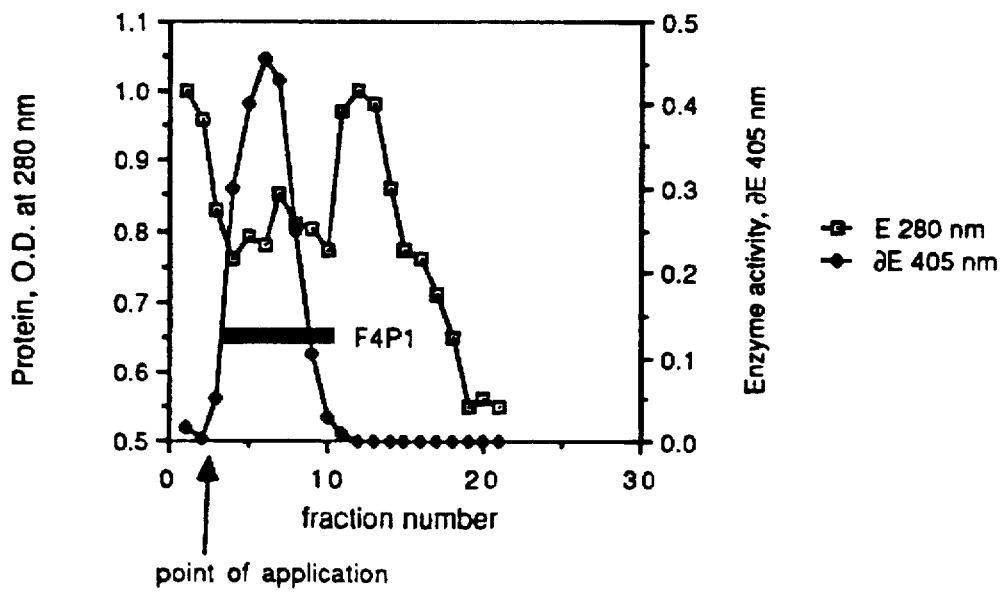

The chromatographic Pool SII fraction was then separated by Pevikon block electrophoresis. In the plastic tray of a horizontal electrophoresis chamber a Pevikon suspension in 0.1M veronal-buffer pH 8.6 was poured to provide a block of 24×13×0.6 cm restricted between plastic edges. Contact was made with the same buffer in the electrode trays by means of 2 Whatman nr. 3 filter paper strips (13×15 cm) soaked in the same buffer. A sample of 12 mg of the Sephadex fraction SII in 120 µl buffer was applied in two slots in the Pevikon block, each being filled with 60 µl of solution. The electrophoretic run was performed at 4° C. for 22 hours at 250 Volts D.C. (the current increased from 22 mA total at the start to 40 mA at the end of the run). After the electrophoretic separation, the block was divided with a sharp knife into 22 sections of 1 cm width. Each section was transferred to a test tube containing 1 ml of 0.1M Tris-HCl buffer pH 8.4. The resulting suspension was centrifuged and the supernatant was removed; after washing the residue with 1 ml Tris-buffer, the supernatant and wash fluid were combined to give the Pevikon block eluates. The enzymatic activity of the eluates was estimated with IPA as the substrate; also, the optical density of the eluates was measured directly in a spectrophotometer at 280 nm to provide a framework for the protein content. A representative separation profile is shown in FIG. 4. On the guide of this profile, the eluates were pooled into three fractions as indicated in the legend to the Figure; these were dialysed and dried by lyophilization. The yields were: SIIP1=1.2 mg, SIIP2=7.0 mg and SIIP3=6.9 mg. The SIIP2 fraction had an activity on IPA of 595 mU/mg, i.e. a 36% increase of specific activity over the starting fraction SII.

Fractions SIIP2 and SIIP3 were also examined by direct intradermal skin-testing (50 µl i.d.) in mite-allergic asthma patients. Fraction SIIP2 produced positive skin reactions at 0.1 µg/ml in the native state, and had undiminished activity after being kept for 10 min at 100° C.; fraction SIIP3 also produced positive skin reactions, but only at 1.0 µg/ml, i.e. was 10 times less potent. Hence, both the IgE-binding potency and the skin-reactivity are associated with the enzyme preparation, but do not require an intact tertiary structure and functional integrity of the enzyme.

c. Isoelectric focusing

Figure 5:
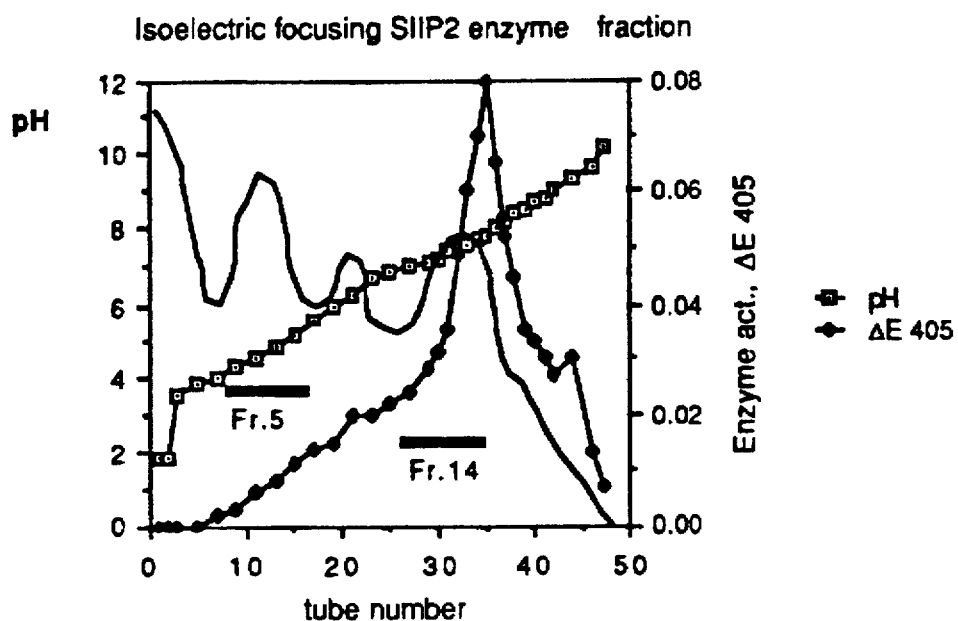

The enzyme pool SIIP2 (6.0 mg) was finally separated by preparative isoelectric focusing essentially according to Chapman and Platts-mills (J Immunol 1980; 125: 587–92) in a sucrose gradient formed in a plastic column (Multiphor, LKB, Sweden). The material was mixed in 110 ml of distilled water, to which was added 2.25 ml of an Ampholine concentrate pH 3.5–10 as the "light" solution. For the "heavy" gradient solution, the same volume of Ampholine concentrate was mixed with 75 ml of distilled water containing 50 grams of sucrose. The electrophoretic focusing was further performed according to the manufacturer's instructions (LKB, Sweden), at 500 Volts D.C. and 4.2 mA for 24 hours at 4° C. Elution was then carried out with the aid of a peristaltic pump at a rate of 1 ml/min. Fractions of 4 ml were collected automatically and the eluates were monitored for UV-absorption at 280 nm, enzyme activity on IPA, and pH-value. A representative separation pattern is shown in FIG. 5, which demonstrates that allergen P1 may be obtained in a more purified state than the classical P1-preparation.

These experiments clearly demonstrate that the major protein components known as "Allergen P1" (M.W.=24 000 daltons) from cultures of *Dermatophagoides pteronyssinus* cannot be distinguished during isolation studies from the major serine protease enzymes monitored by amidolytic or esterolytic assay. Since these methods do not require elaborate skin-testing of human allergic subjects nor complicated antibody assays on their blood sera, this discovery represents an important advance in the isolation and standardization of dust mite allergens.

For further characterization of the allergenic enzyme, a number of physicochemical parameters were established. It was found that the dust mite allergenic enzyme P1 is strongly inhibited by the pancreatic protease inhibitor Trasylol® and by the compounds benzamidine, Soy Bean Trypsin Inhibitor (SBTI) and Lima Bean Trypsin Inhibitor (LBTI). Normal or allergic human blood serum only partially inhibited the esterolytic activity of the enzyme. The molecular size of the allergenic enzyme was estimated at 20–25 000 daltons from ultracentrifugation and by molecular sieving on calibrated Sephadex chromatographic columns (bovine trypsin M.W=24 000 daltons); The molecular size of allergen P1 was likewise reported to be 24 000 daltons. The enzyme exhibits amidolytic and esterolytic activity towards synthetic substrates like IPA and N-p-Tosyl-L-Arginine Methylester (TAMe), but is also capable of hydrolyzing (denatured) proteins and fibrin. The pH-optimum was rather broad at pH 8–10 and the temperature optimum for enzymatic activity was established at 53° C. The enzyme is extremely labile in dilute solution, probably due to adsorption to the glass wall; it is also unstable in more concentrated solution, probably due to autodigestion. These characteristics establish the nature of the allergenic digestive enzyme as a trypsin-like serine esterase excreted by the mite organisms.

2. Isolation of major allergen concentrate by column chromatography on Sephacryl gels a. Extraction of a culture of *Dermatophagoides pteronyssinus* on a mixture of human dandruff and dried yeast.

A quantity of 1994 mg of dry raw material of heat-killed mites grown on leached human dander medium (ARTU Biologicals NV, The Netherlands, lot nr. DP 85) was extracted with stirring for 4 h at 4° C. in a solution of 50 ml 0.1M phosphate 0.9% saline buffer pH 7.4 (PBS)+$10^{-3}$% sodium azide+0.5% Tween-20. The suspension was centrifuged and the residue was re-extracted overnight with 60 ml of the same extractant. Of the combined supernatants (=110 ml), a portion of 10 ml was stored frozen as a reference document at –20° C. The remaining 100 ml supernatant extract was dialysed for 4 h against 2×200 ml of distilled water from Visking dialysis tubing (exclusion limit 10 000 daltons). The nondialyzable retentate portion HMWT was further dialysed exhaustively against 2×1 L water and finally dried by lyophilization to give 152 mg of crude allergen product HMWT, i.e. 7.6% from the crude culture. In a second batch extraction, the yield of HMWT was 12%.

b. Isolation of the protease fraction

A quantity of 100 mg of the allergenic HMWT product was dissolved in in 3 ml PBS pH 7.4 (containing no azide- or Tween-additives) and applied to the top of a column of Sephacryl S-200 gel (Pharmacia AB, Uppsala, Sweden) equilibrated in the same buffer (bed height 43.5 cm, φ2.5 cm). The column was then percolated with the same buffer solution, whereby the optical density at 280 nm of the effluent was monitored continuously and fractions of 6.4 ml volume were collected automatically as eluates. In the eluates, the enzyme activity was measured as follows: 50 µl fraction+140 µl Tris(hydroxymethyl)aminomethane-(TRIS) -HCl buffer (0.1M pH 8.3)+10 µl of the chromogenic tripeptide substrate D-Valyl-L-leucyl-L-arginine-p-nitroanilide-diHCl (VLA, 1.5 µMol/ml) were pipetted into the wells of flat-bottom microtiter plates. The plates were kept for 10 min at 37° C. and the enzymatic reaction was then terminated by adding 50 µl 50% acetic acid to each well. The optical densities of the reaction product p-nitroaniline were then evaluated at 410 nm against appropriate controls in a recording microtiter-plate reading photometer.

Figure 6:
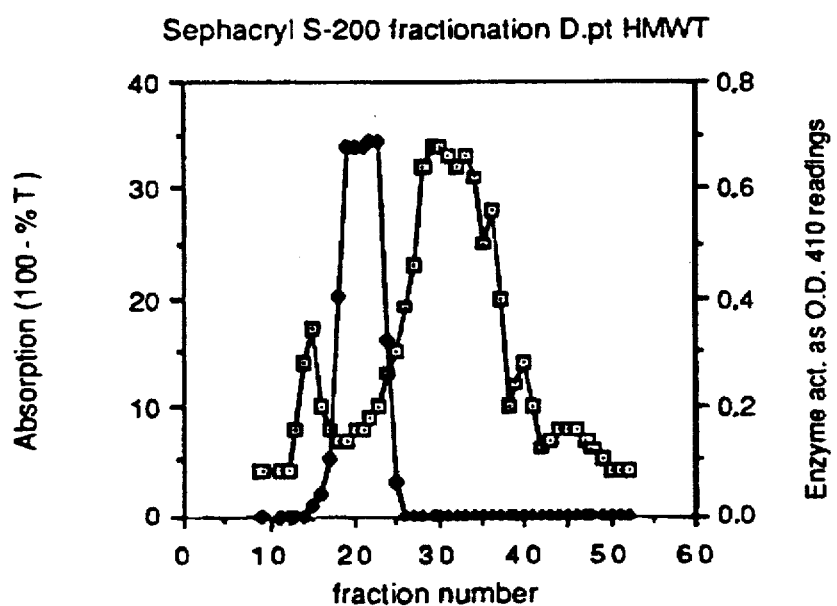

The fractionation diagram and analytical data are shown in FIG. 6. Two Pools of effluent fractions were made as indicated, Pool I constituting the enzyme peak, Pool II the lower-molecular weight material combined with the higher molecular weight substance ("ex P1"). These effluent pools were dialysed against distilled water and dried by lyophilization. The yields were: Pool I=32 mg (=32% in HMWT) and Pool II=82 mg "exP1" (=82% in HMWT). The enzyme activities on VLA were in the ratio HMWT:Pool I:Pool II=10:50:1; the IgE-binding ratios were approximately 4:4:1 (Table J).

3. Isolation by preparative chromatofocusing

A relatively fast one-step preparative procedure for the isolation of the allergenic enzyme from mite cultures is demonstrated by the following example.

Figure 7:
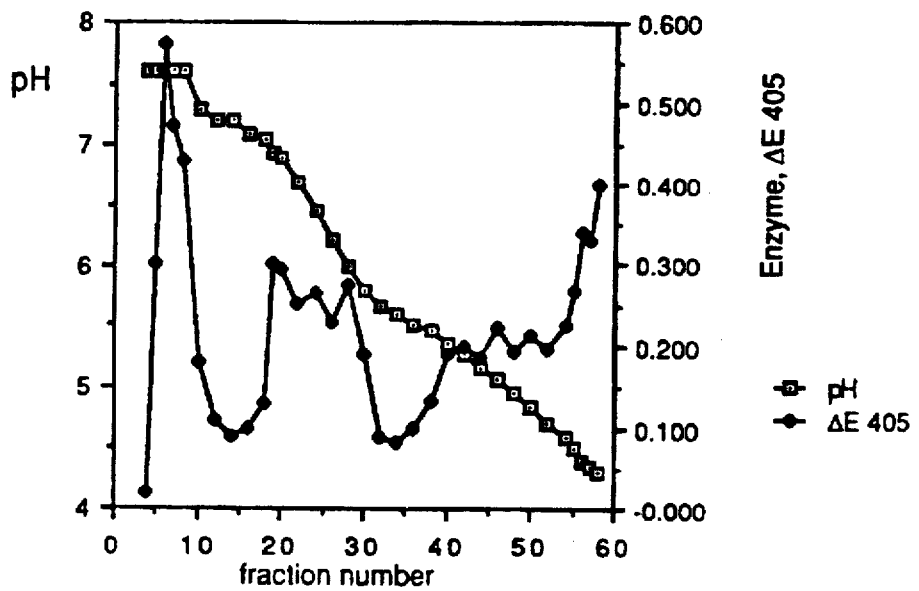

A glass column (0.9 cm φ, 30 cm height) was filled with a Polybuffer Exchanger PBE 94 (Pharmacia AB, Uppsala, Sweden). The column was percolated with 250 ml of a "starting" buffer of 0.025M imidazole-HCl pH 7.4, and a solution of 25 mg *D. pteronyssinus* HMWT in 3 ml of this buffer was applied to the top of the column. Elution was then performed with Polybuffer 74 (Pharmacia AB, Uppsala, Sweden) adjusted to pH 4.0 with 0.5M HCl and diluted 1:8 with distilled water. The effluent was collected automatically in 3 ml fractions, which were screened for pH-value and enzymatic conversion of the chromogenic tripeptide substrate VLA. A representative elution and analysis pattern is shown in FIG. 7.

4. Isolation by affinity chromatography

For this experiment, an affinity support was made by covalent coupling of Sepharose 4B beads (Pharmacia AB, Uppsala, Sweden) to the polyvalent bovine proteinase inhibitor BPTI by means of cyanogen bromide at pH 11.0. The source of BPTI was the commercial product Trasylol® (Bayer AG, Germany); 20 000 inhibitor units KIE were chemically coupled to 75 ml of packed Sepharose 4B. After the coupling reaction, the affinity support was treated briefly with ethanolamine to inactivate unreacted imino-groups, and the support was finally washed with 0.01M phosphate buffer pH 7.4 and poured into a chromatographic column of 1.5 cm φ and 25 cm height. To this column was applied a solution of 10 mg *D. pteronyssinus* HMWT in 1 ml phosphate buffer as described in Example VIII.1.

The column was eluted in three steps.

A. Elution was first performed with 0.01M phosphate buffer pH 7.4, which served for the absorption of the major mite allergen to the immobilized BPTI. The material in the breakthrough peak was collected, dialysed and freezedried to give 4.5 mg of product Pool I. The column was then percolated with an extra 250 µl of the same buffer for complete rinsing.

b. Elution was done with 0.1M glycine-HCl buffer pH 3.0 for desorption of the major mite enzyme bound reversibly to the inhibitor support. The eluted fractions were again combined, dialysed against distilled water, and freezedried to give 2 mg of product Pool II.

c. The column was finally eluted with a solution of 3M KBr (in another experiment with 3M KCNS) to produce 2 mg of the final product Pool III.

The enzyme activity on the substrate N-p-Tosyl-L-Arginine-Methylester (TAMe) was established with chromotropic acid as follows:

1 ml of each Pool fraction before freezedrying was mixed with 0.3 ml 1% TAMe in 0.1M phosphate buffer pH 7.4 and the mixture was kept at 37° C. for 60 minutes. The enzymatic reaction was terminated by adding 0.5 ml 15% trichloroacetic acid. From the solution, 1 ml was then transferred to a tube containing 0.1 ml 2% $KMnO_4$, followed by 0.2 ml $Na_2SO_3$ and 4 ml of Na-chromotropic acid (Merck, Darmstadt, Germany) in conc. $H_2SO_4$. The mixture was heated for colour development for 15 min at 100° C., cooled in ice-water and evaluated against a standard curve by reading the optical density in a spectrophotometer at 580 nm.

No enzyme activity was detected in the Pool I preparation, which nevertheless had the highest protein content. Similarly, no enzyme activity was associated with the Pool III preparation. The bulk of the protease activity eluted in the Pool II product with the acid glycine-HCl buffer and corresponded to the major allergen Der p I. This material comprised about 6% of the total protein in the original *D. pteronyssinus* HMWT preparation.

5. Standardization

A major problem in the production and pharmaceutical validation of allergenic extracts for the diagnosis and therapy of allergic disease in man concerns their proper dosage and standardization. Current methods depend on the assay of allergenicity by direct skin-testing in allergic patients and on the (inhibition-of) binding of specific (IgE-) antibodies present in their blood serum. The discovery of the enzymatic properties associated with the major allergens in such extracts now also permits an easy and direct assessment of the allergenic potency. As an example, a series of allergenic extracts were prepared from various different batches of crude materials in current use as source products; these concerned a culture of *D. pteronyssinus* on ox liver powder produced by a British manufacturer (BRL), several batches of cultures on leached human dandruff powder from a Dutch producer (ARTU), a preparation consisting of microscopically pure mite bodies from an American firm (BioPol), and a mite culture extract produced by the World Health Organization and arbitrarily assigned 100 000 International Units (I.U.)/mg. For the classical assay by RAST-inhibition, sera were pooled from Dutch asthma patients with high titers of specific anti-mite IgE-antibodies in the blood serum. As solid phase, cellulose discs coupled with commercial mite preparations were purchased from Pharmacia AB, Uppsala, Sweden.

Figure 8:
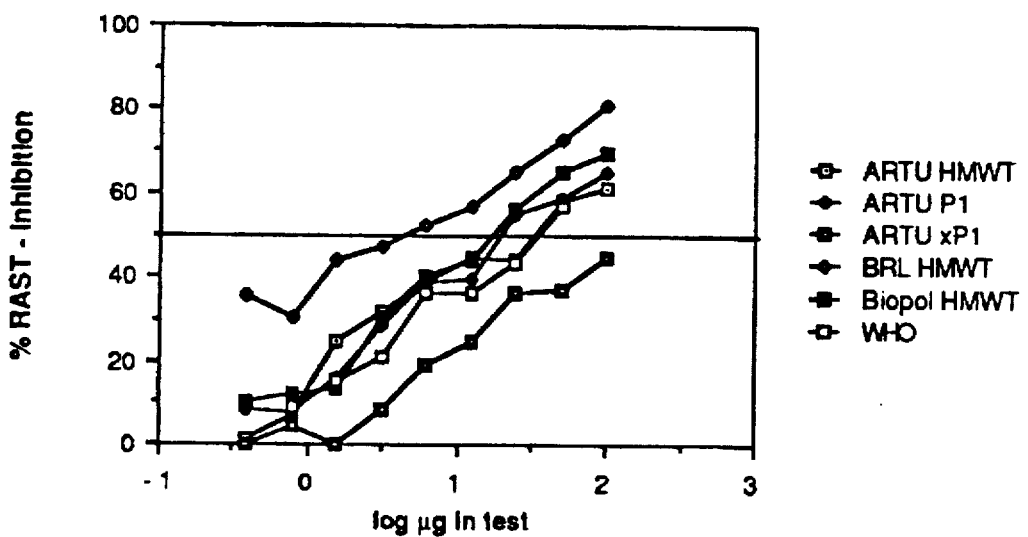

A comparative series of RAST-inhibition dose-response curves are shown in FIG. 8. The specific activity of the same preparations on the synthetic substrate VLA were also established (Table J). The results were converted into International Units in relation to the WHO Standard Preparation 82/518. These data have been listed in Table K.

Table J. Amidolytic enzyme activity on VLA, in mU/mg lyophilized product (=|=E 405/min×1000×0.003492×µg in test system) and IgE-binding capacity, in µg for 50% RAST-inhibition interpolated from FIG. 8 or in Units/mg (=1000× 1µg for 50% inhibition) in order of increasing potency.

TABLE J

| Preparation | Enzyme mU/mg | RAST-inhibition µg/50% | U/mg |
|---|---|---|---|
| D.pteronyssinus, HMWT from culture on hum.dander, 1st batch | 30.3 | 23.8 | 42.0 |
| D.pteronyssinus, P1 (= Der p I), 1st batch | 157.0 | 24.0 | 41.7 |
| D.pteronyssinus, P1-depleted (= ex Der p I), 1st batch | 3.2 | >100 | <10 |
| D.pteronyssinus, HMWT from culture on hum.dander, 2nd batch | 50.3 | | |
| D.pteronyssinus, P1 (= Der p I), 2nd batch | 96.4 | | |
| D.pteronyssinus, P1-depleted (= ex Der p I), 2nd batch | 2.3 | | |
| D.pteronyssinus, HMWT from culture on hum. dander, 3rd batch | 73.3 | | |
| D.pteronyssinus, HMWT from culture on ox liver powder | 138.3 | 4.9 | 204.1 |
| D.pteronyssinus WHO-Standard 82/518 | 152.0 | 32.3 | 30.96 |
| D.pteronyssinus clean mite body HMWT (= Der p II) | 0.5 | 16.4 | 60.98 |
| D.farinae clean site body HMWT (Der f II) | 0.1 | | |

Table K. "Standardization" of allergenic preparations from *D. pteronyssinus* by inhibition of IgE-binding from human allergic serum ("RAST-inhibition") or by amidolytic assay, expressed in the defined unitage of 100 000 International Units/mg for the WHO-Standard.

TABLE K

| | International Units/mg | |
|---|---|---|
| Preparation | Amidolytic Potency | RAST-inhibition |
| WHO - standard 82/518 | 100 000 | 100 000 |
| BRL - HMWT | 91 000 | 659 000 |
| ARTU - HMWT | 19 930 | 136 000 |
| ARTU - P1 | 103 290 | 135 000 |
| ARTU - ex P1 | 2 110 | <30 000 |
| BIOPOL - whole body | 330 | 197 000 |

Correlation coeff. r = 0.36
P > 0.25, not significant

It follows from these results that the enzymatic properties of the major allergens in extracts of *Dermatophagoides pteronyssinus* may be used as a marker of the overall allergenic potency of extracts of the excrete, but not of the pure mite bodies, which contain the antigenically distinct minor allergen Der p II. Since the enzymatic properties depend on an intact and thermolabile tertiary structure, whereas the skin-reactivity and IgE-binding properties obviously depend on the thermostable secondary protein structure, it follows that enzyme determination for the purpose of standardization must be performed on freshly prepared and coldstored extracts.

EXAMPLE IX

Isolation of Allergenic Kallikrein Enzymes from the Skin (Dander) and Urine of the Domestic Cat, *Felix domesticus*

This Example shows that the major cat allergen is identical to, or closely associated with the kallikrein enzyme activity detectable in both cat dander and urine.

1. Isolation of "Cat Allergen 1" (=Fel d 1) from cat dander according to Ohman et al.

a. Preparation of the active allergenic extract 10 grams of acetone-treated mixed cat dander source material (ARTU biologicals, Lelystad, Holland) was extracted 3 times with 70 ml each of PBS/Tween-20 buffer, pH 7.4. The centrifuged and combined extracts were dialysed from Visking tubing (exclusion limit 10 000 daltons) for 24 hours against three changes of distilled water and the nondialysable retentate was finally lyophilized to give 546 mg of the HMWT preparation, i.e. a yield of 5.5% from crude cat dander.

b. Fractionation 25 mg of cat dander HMWT was dissolved in 5 ml phosphate buffer 0.01M, pH 7.4 and applied to a 1.5×30 cm chromatographic column packed with DE 52 (Diethylaminoethyl-cellulose, Whatman) equilibrated in the same buffer and initially percolated with the same buffer. After passage of 150 ml, down-flow elution was continued with the same buffer mixed with a linear salt-gradient of 0.0M up to 0.4M NaCl. In the eluted fractions enzyme activity was assayed for VLA-conversion in tubes by incubating 200 µl fraction, 700 µl 0.1M Tris-HCl buffer pH 8.2, 100 µl VLA (1.5 µMole/ml) for 75 min at 37° C. The reaction was terminated by the addition of 100 µl 50% acetic acid, and the optical densities were finally read at 410 nm in microtiter plates. Fractions off the column between 0.10M and 0.14M NaCl were pooled according to the enzyme peak and were lyophilized. The freezedried product was taken up in 4 ml distilled water and applied to a 2.5×90 cm column of Sephadex G75 in PES pH 7.4; elution was done with the same solvent. Aliquot portions of the effluent fractions were assayed for enzyme activity and the corresponding kallikrein enzyme peak was collected. The column had in a preceding run been calibrated with molecular markers Ribonuclease A (MW=13700), Chymotrypsinogen A (MW=25000), Ovalbumin (MW=43000) and Dextran Blue (MW>>500 000). The elution volume of the cat dander enzyme was interpolated on the calibration curve and gave an apparent molecular weight of M=40 000 daltons. Examination in the ultracentrifuge in a sucrose-density gradient at 40 000 r.p.m. for 24 hours gave a corresponding $S_{20,w}$ value of 2.5 S. The temperature optimum of the enzyme for VLA-conversion at pH 8.2 was established at 52° C., the pH-optimum at 37° C. was at pH 9.0.

Figure 9:
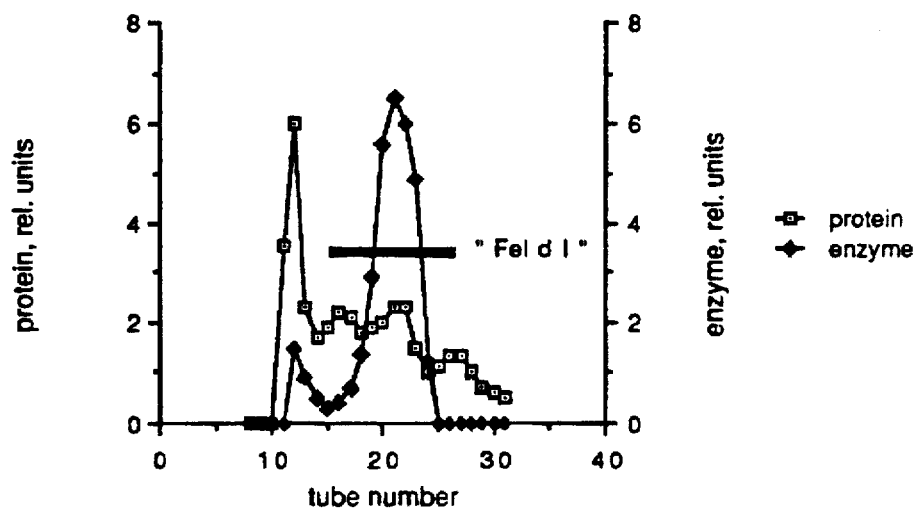

Although these studies showed that cat urinary kallikrein and "cat allergen 1" could not be distinguished, the cumbersome and low-yield isolation method of Ohman et al. was abandoned in favour of a one-step isolation technique from cat dander HMWT by molecular sieving on a column of Sephacryl S-300, along similar lines as discussed for the D per I allergen in EXAMPLE I.2.b. A representative elution pattern is shown in FIG. 9. In a typical isolation experiment, 4 grams of cat dander acetone powder (ARTU Biologicals, Lelystad, The Netherlands) were extracted as described above, to yield 215 mg of crude allergen HMWT (i.e. 5.4% in source material). Chromatographic separation on Sephacryl S-300 then produced a recovery of 56% of Cat Allergen 1 from HMWT, i.e. 3% in the source material. The ratio of enzyme activities in mU/mg on VLA was HMWT:Cat allergen 1:Cat "ex 1"=7.7:5.7:0.6, or 13:10:1. The enzyme only poorly converted the trypsin substrate IPA.

2. Isolation of allergenic enzyme from cat dander by affinity chromatography

Figure 10:
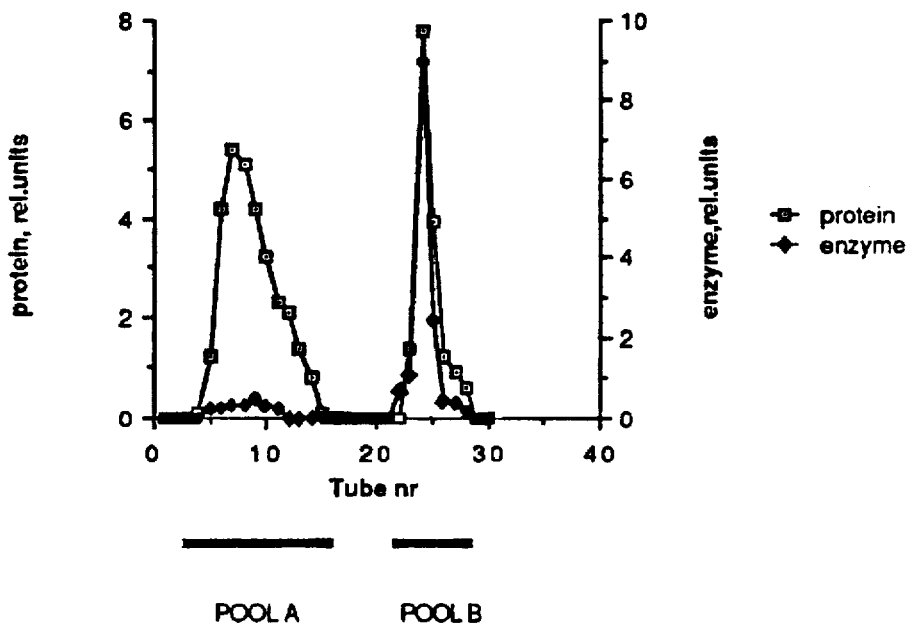
Figure 11:
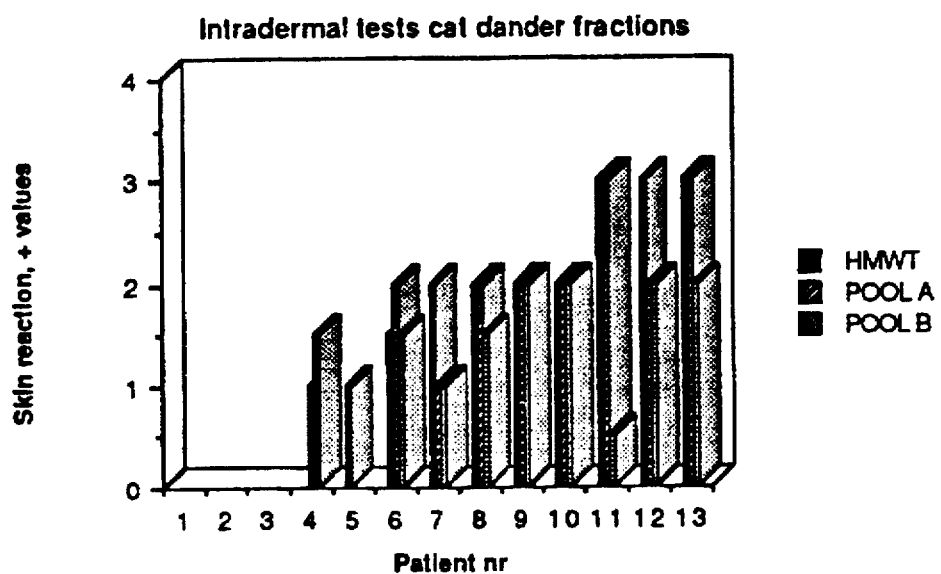

A chromatographic affinity support was prepared by reacting Sepharose beads (Pharmacia AB, Uppsala, Sweden) with the enzyme inhibitor benzamidine by means of the coupling agent cyanogen bromide at pH 11. The gel support was washed with PBS pH 7.4 and poured into a glass column (φ 0.9 cm, height 25 cm). A solution of 25 mg lyophilized cat dander HMWT in 10 ml PBS was slowly sieved through the column, followed by elution with PBS. Protein content and enzyme activity on VLA were monitored in the breakthrough effluent, as shown in FIG. 10 (Pool A). The column was then percolated with a glycine-HCl buffer (0.1M, pH 2.9) and the effluent was similarly analyzed and combined (FIG. 10, Pool B). The protein concentration in Pools A and B, established with the Lowry reagent, was 0.6 mg/ml and 0.43 mg/ml, respectively. The intradermal skin test results obtained with these concentrates in cat-allergic patients are shown in FIG. 11. These data show that, although the "cat allergen 1"—now identified in the scientific literature as the major allergen of cat dander—coincides with the kallikrein enzyme from the dander, it is not the sole skin-reactive (or IgE binding) antigen for cat-allergic individuals.

3. Isolation of major allergenic kallikrein enzymes from cat urine

The urine of female cats (200 ml) was obtained by sterile catheterization. The sample was filtered and solid di-sodium ethylenediaminotetraacetic acid EDTA was added to a final concentration of 0.001M. The solution was then dialysed against distilled water and lyophilized to give 245 mg of crude urinary allergen HMWT, i.e. 1.11 grams/L.

A sample of 75 mg of this product HMWT was passed through a column of Sephadex G 200, 90×2.5 cm, in borate-buffered saline BBS pH 8.0; fractions of 6 ml were collected automatically. The column fractions were monitored for enzyme activity with the chromogenic tripeptide substrate VLA: 0.6 ml Tris-HCl buffer, 0.3 ml eluate, 0.1 ml VLA-solution (1.5 μMole/ml) were incubated at 37° C. in the cuvette of a photometric reaction rate analyzer, and the △ at 405 nm was recorded in the 3rd minute as a parameter for enzyme activity. Fractions were pooled as specified in the legend to FIG. 13. The recovered preparations after dialysis and freezedrying were slightly hygroscopic and were taken up in 1.5 ml saline for evaluation of the IgE-binding power by RAST-inhibition, using a pool of 12 sera of cat-allergic patients. Graphs were constructed as exemplified for mites in FIGS. 3 and 8, and the points of 50% inhibition of IgE-binding were obtained by interpolation; the results have been incorporated in FIG. 12.

The quantitative relationships among Pools I–III were:

RAST-inhibition:Pool I:II:III=4:30:1

Enzyme activity on VLA:Pool I:II:III=1:30:0

Figure 12:
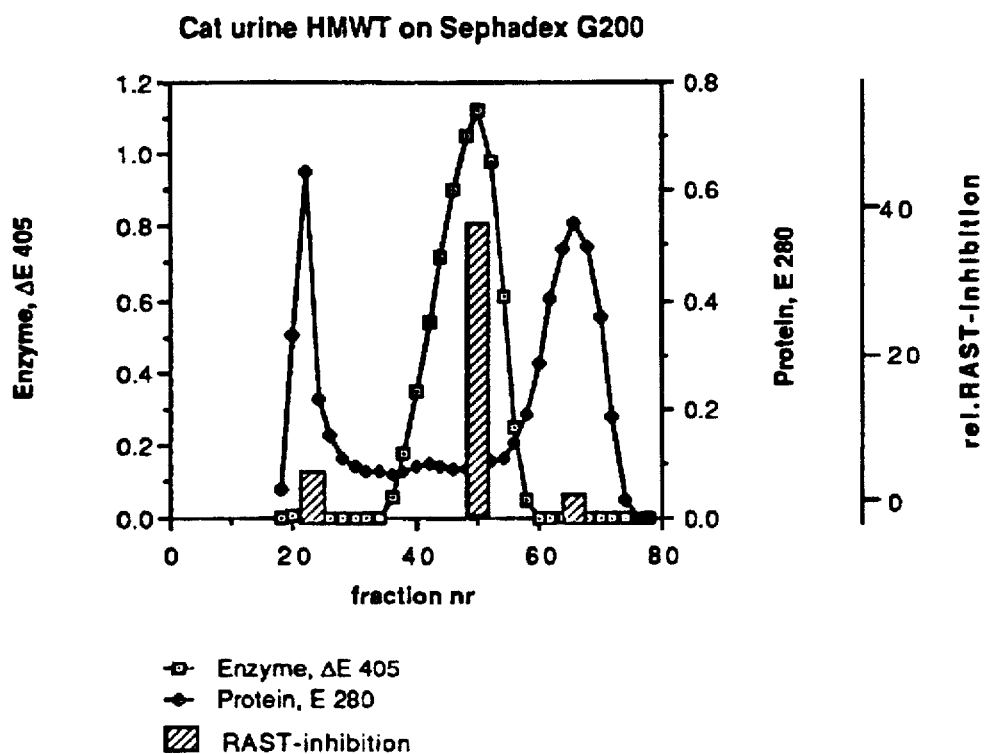
Figure 13:
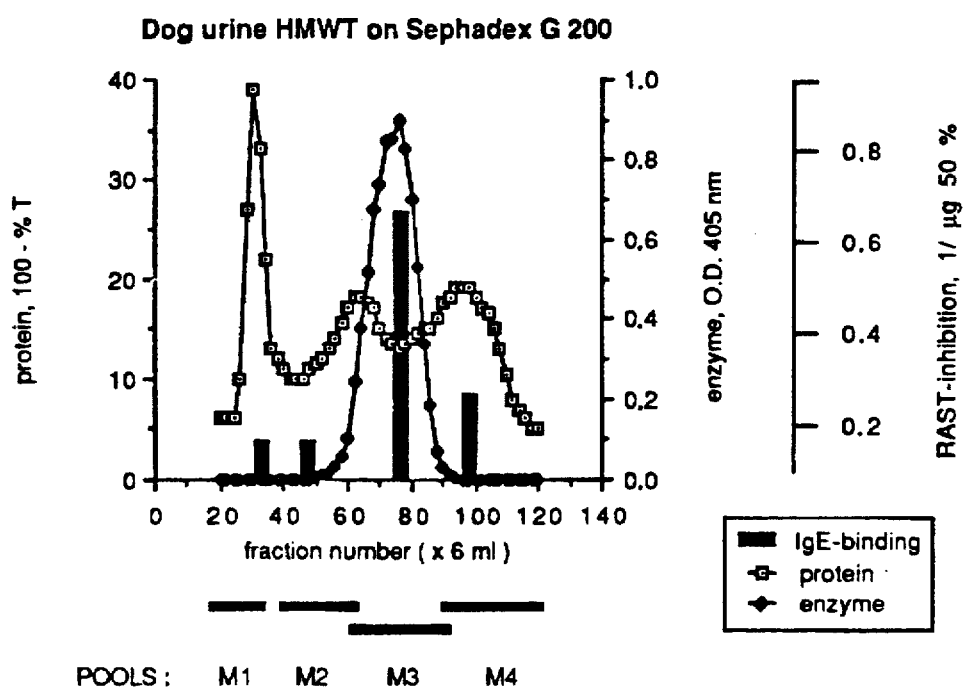

Cat urine HMWT had a specific activity on VLA of 30.0 mU/mg, i.e. 4 times higher than cat dander HMWT. Cat urine HMWT had a low specific activity towards the substrate IPA and converted the chromogenic tripeptide substrate <Glu-Gly-Arginine-p-nitroanilide for classical urokinase to the extent of only 10% of VLA. Cat urinary kallikrein in the active state, but also after heating for 10 minutes at 100° C., evoked positive wheal and flare reactions in the skin of cat-allergic subjects at 20 μg/ml, i.e. at 5× higher concentration than the allergenic enzyme from cat dander (FIG. 12). Although cat urinary kallikrein therefore represents a major allergen for man, the antigenic molecule is recognized by way of its primary or secondary structure. Freshly prepared urinary allergens standardized on the basis of their kallikrein activity hence maintain their unitage even after the enzyme has become denatured.

EXAMPLE X

Isolation of Allergenic Kallikrein Enzymes form the Skin (Dander) and Urine of the Dog, *Canis familiaris*

1. Isolation of a "Dog Allergen 1" equivalent from dog dander a. Preparation of an active allergenic extract Dry acetone-washed skin flake powder from mixed dog breeds was purchased from ARTU Biologicals, Lelystad, The Netherlands (lot nr. 86M11/105-03); 5 grams of the dry powder was extracted twice with stirring in 100 ml 1% NaCl/1% phenol. The combined centrifuged extracts were dialysed from Visking tubing (exclusion limit 10 000 daltons) and lyophilized to give 135 mg of crude dog allergen HMWT, i.e. 2.7% from the source material.

b. Fractionation 75 mg dog dander HMWT in 5 ml PBS pH 8.0 was sieved through a 2.5×45 cm column of Sephadex G 200 in the same solvent; 6 ml fractions were collected, and the enzyme activity of the eluates was assayed with the VLA-substrate:100 μl fraction, 10 μl VLA-solution (1.5 μMole/ml) and 90 μl 0.1M Tris-HCl buffer pH 8.2 were incubated for 60 min at 37° C.; the reaction was then terminated by the addition of 100 μl 50% acetic acid and the resulting colour was read at 410 nm read in a microtiter plate photometer. The elution pattern and distribution of protein, enzyme activity and IgE-binding was closely similar to the results obtained with cat urine (see FIG. 12). Two pool fractions were made, namely the enzyme peak (POOL I) and the combined remaining fractions (POOL II), which were isolated in the dried non-hygroscopic state to give 27 and 19 mg respectively, i.e. 36% and 25% in HMWT; total recovery 61%. Dog Allergen 1 (or Can f I) may therefore be obtained from dry dog dander in a yield of approximately 1%.

The quantitative relationships were:

Enzyme activity on VLA (in mU/mg):HMWT:Allergen 1:"ex 1"=24:44:6 or 4:7.3:1

RAST-inhibition in µg/ml:HMWT:Allergen 1:"ex 1"=11.4:55.5:6.7 or in order of potency (reciprocals) 0.088:0.149:0.018=4.9:8.3:1

It follows again that the antigenic dog dander "Allergen 1" and the (skin) kininogenase enzyme are identical or closely related.

One-step isolation of the major enzyme allergen on columns of Sephacryl S-200 or S-300 was successfully accomplished as has been described for Cat Allergen I (EXAMPLES II.1.b). By this method, the major dog dander allergen was isolated from the crude source material in a yield of 0.5%.

b 2.Isolation of major dog urinary allergens

Uncontaminated sterile dog (beagle) urine was obtained by catheterization. To the urine was added 20 g sodium benzoate per L (to reduce the volumes to be handled, and because both (house dust) allergens and urinary kallikreins are known to be adsorbed to benzoic acid). The clear solution was acidified with 4N HCl to pH 4.0.the precipitate was filtered, dissolved in acetone and left overnight in the cold. The precipitate was then centrifuged, suspended in PBS and the pH adjusted to 8.0. The solution was finally dialyzed and freezedried. The yield was 204 mg/L urine for male dogs, code MHMWT, and 456 mg/L urine for bitches, code FHMWT. The specific enzymatic activities were:

on the kallikrein substrate VLA:MHMWT=101 mU/mg; FHMWT=92 mU/mg on the trypsin substrate IPA:MHMWT=11.3 mU/mg; FHMWT=6.4 mU/mg For further purification, 100 mg of each product (MHMWT or FHMWT) was then fractionated by molecular sieving through 80×2.5 cm columns of Sephadex G-200 in PBS buffer pH 8.0. The columns were percolated with the same buffer and effluent fractions of 6 ml were collected automatically. The enzyme activity in 25 µl aliquots of the fractions was assayed with VLA as the substrate in a microtiter assay as described in the preceding EXAMPLES. Fractions were also examined for inhibition of IgE-binding from a pool of human dog-allergic sera (diluted 1:10, RAST-dog value 27% binding). The elution diagram is shown for the example of MHMWT in FIG. 13. RAST-inhibition dose-response plots of the pooled major MHMWT-fractions were constructed as described and illustrated in FIGS. 3 and 8, from which the point of 50% inhibition was found by interpolation. The yield of the pooled fractions in order of decreasing molecular size was: M1=16 mg, M2=21 mg, M3=11 mg, M4=7 mg, recovery 55%.

The quantitative relationships were:

Kallikrein activity by amidolysis:M1:M2:M3:M4= 1:3:70:28

IgE-binding activity:M1:M2:M3:M4=1:2:33:17

The major allergen and the VLA-hydrolyzing enzyme Can f I therefore coincide, and occur in a proportion of about 22 mg/L of male dog urine. The enzyme was not inhibited by normal human serum.

EXAMPLE XI

Isolation of Major IgE-Binding Allergenic Enzyme from Urine of the Mouse, *Mus musculus*

Clinical phenomena known as "occupational animal allergy" occur quite frequently among professional people working with small animals in experimental laboratories. The disease symptoms have been attributed to powerful atopic allergens in the inhaled air and derived from the danders and, especially, the urine of such animals. The urinary allergens of the mouse and the rat have been studied in some chemical and immunological detail (e.g. Schumacher MJ. Mol Immunol 1980; 17: 1087–95). This EXAMPLE demonstrates that the major mouse urinary allergens are identical to, or closely associated with, mouse urinary kallikrein.

Figure 14:
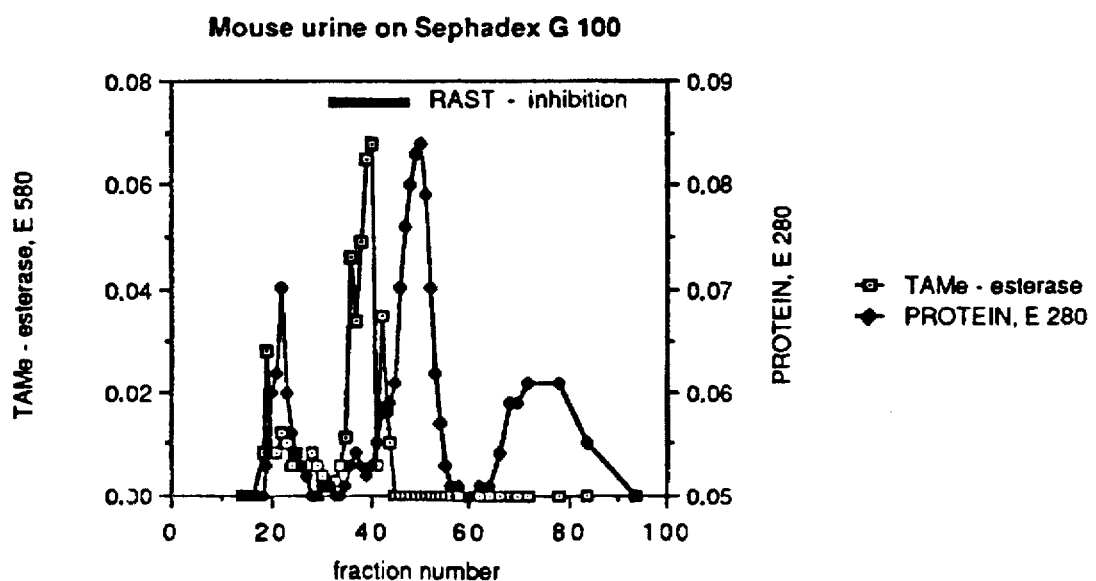

In a representative experiment, urine was collected from inbred female Swiss mice sacrificed after having served for experimental antibody production. The urine was dialysed against distilled water from Visking dialysis tubing (exclusion limit 10 000 daltons) and lyophilized to produce the non-hygroscopic non-dialysable material HMWT. A sample of 20 mg HMWT was fractionated by gel filtration on a 90×2.5 cm column of Sephadex G 100 in saline (=0.9% NaCl). Material was eluted with the same solvent, and 6 ml effluent fractions were collected automatically. Fractions were analyzed for inhibition of specific IgEbinding, using the serum of a specifically sensitized atopic laboratory worker and discs coupled chemically to mouse urine HMWT. Aliquots were also examined for esterolytic activity, using the substrate N-p-Tosyl-L-Arginine Methylester (TAMe) as follows: 1 ml of eluate was incubated with 3 mg TAME (British Drug Houses, Poole, England) in 0. 5 ml 0.1M phosphate buffer pH 7.5 for 60 minutes at 37° C. The methanol released was then determined colorimetrically with a conventional chromotropic acid-$H_2SO_4$ reagent. The distribution of the enzyme activity and the major IgE-binding peak in the elution diagram is shown in FIG. 14. As demonstrated in the previous EXAMPLES, the kallikrein enzyme of mouse urine again coincides closely with the major allergenic components. However, although the enzyme activity was completely abolished by heating for 10 min at 100° C., the IgE-binding capacity remained virtually unchanged.

EXAMPLE XII

Miscellaneous Animal (Insect) Allergens

The medical literature is replete with clinical descriptions of patients sensitized to specific allergens associated with insects or animals in their personal or professional environment. Sensitization to particular animal or insect excerta or secreta may under certain conditions become widespread, as exemplified by epidemiological studies of allergies to cockroaches in the U.S.A. and to the bug *Trogoderma angustum* in W.Berlin. The investigations pertaining to the present Invention have been extended to an examination of the relationships between the major allergens in these cases and the—sometimes very powerful—proteolytic enzymes detectable in the relevant allergenic extracts. In these cases, similar conclusions of allergen—enzyme identity or—association have been reached as discussed in detail in the foregoing EXAMPLES. Table L lists some of the hitherto undescribed specific amidolytic activities of important allergenic materials.

TABLE L

| Animal product | VLA, mU/mg |
|---|---|
| Cockroach, Sephacryl enzyme fraction | 287.0 |

TABLE L-continued

| Animal product | VLA, mU/mg |
| --- | --- |
| Locust excreta HMWT | 1170.0 |
| Locust excreta, Sephacryl enzyme fraction | 1299.0 |
| Musca domestica, HMWT | 25.0 |
| Pigeon excreta, HMWT | 17.8 |
| Trogoderma angustum, HMWT | 2235.0 |

LEGENDS TO THE FIGURES

FIG. 1

Correlation between capacities of 74 different house dust extracts to bind IgE-antibody in pool-serum of mite-allergic patients (expressed as log reciprocal of 50% RAST-inhibition), and the protease activity in corresponding extracts as measured with the substrate I.P.A.

FIG. 2

Sephadex G100 gel filtration of 25 mg D.pt. HMWT (column 90×1.6 cm) in borate-buffered saline. Void volume emerges in tube 8. The eluting position of the molecular markers Bovine Serum Albumin (MW=65 000) and Cytochrome-c (MW=12 500) are indicated by arrows. The horizontal bars show the eluting position of the fractions (3–4) and the chosen fraction F4 reported by Chapman and Platts-Mills (Clin exp Immunol 1978; 34: 126–36) on the basis of maximum skin-reactivity and direct IgE-binding. Three pools were made, comprising the contents of tubes 8–13 (Pool SI), 14–21 (Pool SII) and 22–34 (Pool SIII).

FIG. 3

RAST-inhibition of *Dermatophagoides pteronyssinus* HMWT and HMWT heated for 10 min at 100° C., together with the Pool fractions off a Sephadex G100 column according to Chapman and Platts-Mills. Serum #810809 was used, dil. 1:4, Pool conc.: 10 mg/ml, 50 µl per tube in a 2-step dilution series, starting undiluted 1:1.

FIG. 4

Pevikon-block electrophoresis of fraction SII as described in the text; positive electrode (anode) on the right. The horizontal bar marks the fraction F4P1 reported by Chapman and Platts-Mills (Clin exp Immunol 1978; 34: 126–36) as the major RAST-binding and skin-reactive allergen. Separated fractions were combined into 3 Pools, viz: Pool SIIP1 (tubes 1–5), Pool SIIP2 (tubes 6–12) and SIIP3 (tubes 13–22).

FIG. 5

Preparative isoelectric focusing of the purified allergen fraction SIIP2 in a sucrose-density gradient. The major enzyme peak focusses between pH 6.6–7.5 and corresponds to fraction 14 of Chapman and Platts-Mills (J Immunol 1980; 125: 587–92). protein concentration in the eluted fractions was too low to be measured by way of the usual assay systems; the thin undotted line represents the protein pattern published by Chapman and Platts-Mills. The bars indicate the fractions identified by these authors as immunochemically identical components, both having an apparent molecular weight of 24 000 daltons and carrying the major antigenic and skin-reactive properties; these fractions have collectively been designated as *Dermatophagoides pteronyssinus* antigen P1.

FIG. 6

Column fractionation of 100 mg lyophilized *Dermatophagoides pteronyssinus* HMWT product on Sephacryl S-200. For conditions see text. The single enzyme peak was pooled to give the Pool I fraction; the protein fractions to the left and the right were pooled to give the Pool II product (="ex P1").

FIG. 7

Chromatofocusing of a 25 mg sample of HMWT preparation of *D. pteronyssinus* culture. The fractions 20–30 comprise the major allergenic enzyme component.

FIG. 8

Standardization of different preparations of *Dermatophagoides pteronyssinus* extract by inhibition of specific IgE-binding in the radioallergosorbent test (RAST). The quantity for 50% inhibition of serum IgE-binding is read at the intersection with the individual dose-response curves.

FIG. 9

Isolation of major cat dander allergen Fel D I by molecular sieving of 100 mg cat dander HMWT through a 2.5 cm ϕ×40 cm bed height column of Sephacryl S-300. The black bar indicates the eluted fractions pooled to give the major enzymatic allergen.

FIG. 10

One-step isolation of the major allergenic cat dander enzyme by affinity chromatography on Sepharose-benzamidin.

FIG. 11

Results of intradermal tests in cat-allergic patients with cat dander Pools A and B isolated by affinity chromatography on Sepharose-benzamidine. The solutions were sterilized by filtration through Amicon® filters and tested at 4.0 µg/ml, the injected volume being 50 µl. The HMWT-product was an unfractionated dialysed commercial cat dander extract at the same concentration.

FIG. 12

Molecular sieving of cat urine HMWT on Sephadex G 200 column (90×2.5 cm) and distribution of the protein concentration, kallikrein activity and RAST-inhibitory power over the eluted fractions. RAST-inhibition in relative units, i.e. in reciprocal dilution of lyophilized pool fraction (in 1.5 ml 0.9% NaCl) for 50% inhibition of IgE-binding from a pool of cat-allergic human blood sera. Three pools were made, comprising the eluates from tubes 15–35 (Pool I), 36–59 (Pool II) and 60–79 (Pool III).

FIG. 13

Gel filtration of 100 mg of male dog urine MHMWT on a 80×2.5 cm column of Sephadex G 200 in phosphate buffered saline pH 8.0. Effluent analysed for enzymatic activity on chromogenic tripeptide kallikrein substrate VLA in microtiter plate assay, for total protein (O.D. at 280 nm) and for specific IgE-binding power (reciprocal of µg pool fractions M1–M4 for 50% inhibition) from 50 µl of human dog-allergic pool serum, using dog urinary MHMWT-discs.

FIG. 14

Gel filtration of 20 mg mouse urine HMWT on a 90×2.5 cm chromatographic column of Sephadex G 100 and eluted with 0.9% NaCl. Esterolytic activity and IgE-binding potential ("RAST-inhibition") indicated.

I claim:

1. A method of hydrolyzing amide and/or ester linkages in a substrate, comprising: contacting a substantially purified form of an atopic allergen having protease properties with a substrate having amide and/or ester linkages to thereby hydrolyze said linkages, wherein said allergen is isolated from mammalian and non-mammalian excrement sources, and is capable of hydrolyzing proteins and split substrates specific for enzyme active sites.

2. Method according to claim 1, wherein the allergen originates from mammals and is isolated from the group consisting of saliva, sweat, dry skin scales, and urine, said allergen being capable of splitting low-molecular weight substrates specific for tissue kallikreins.

3. Method according to claim 1, wherein the substrates are peptide derivatives comprising an amino acid or amino acid sequence designed to fit the active site of proteases with the substrate-specificity of human and bovine trypsin and chymotrypsin, or designed to fit the active site of proteases with the substrate-specificity of animal glandulary kallikreins.

4. Method according to claim 3, wherein the peptide derivatives are the naphthylamides of monoamino, dipeptide, tripeptide or oligopeptide compounds.

5. Method according to claim 3, wherein the substrates are alkylesters of naphthyl, p-benzoyl or p-tosyl chromogenic conjugates of monoamino, dipeptide, tripeptide or oligopeptide derivatives comprising an amino acid or amino acid sequence designed to fit the active site of proteases with the substrate-specificity of human and bovine trypsin and chymotrypsin or with the substrate-specificity of animal glandulary kallikreins respectively.

6. Method according to claim 1, wherein the enzymatic substrates have been conjugated to a fluophoric group.

7. Method of establishing the allergenic potency of environmental dust samples or individual allergenic preparations, comprising: preparing an aqueous extract of an environmental allergen or allergen preparation, and quantitatively measuring the protease activity of said aqueous extract towards different specific substrates, said substrates having amide and/or ester linkages.

8. A kit for establishing the allergenic presence of environmental dust samples or individual allergenic preparations, comprising: a carrier containing a substrate having amide and/or ester linkages, said carrier adapted to detect the protease activity of an aqueous extract of an environmental allergen, or of an allergenic preparation.

9. A kit according to claim 8, wherein the carrier is in the form of a strip.

* * * * *